US010004923B2

United States Patent
Mougin et al.

(10) Patent No.: US 10,004,923 B2
(45) Date of Patent: *Jun. 26, 2018

(54) NEUTRALISED CATIONIC POLYMER, COMPOSITION CONTAINING SAID POLYMER AND A COSMETIC TREATMENT METHOD

(75) Inventors: Nathalie Mougin, Paris (FR); Gwenaëlle Jegou, Livry Gargan (FR)

(73) Assignee: L'OREAL, Paris (FR)

(*) Notice: Subject to any disclaimer, the term of this patent is extended or adjusted under 35 U.S.C. 154(b) by 1274 days.

This patent is subject to a terminal disclaimer.

(21) Appl. No.: 11/988,179

(22) PCT Filed: Jun. 30, 2006

(86) PCT No.: PCT/FR2006/001547
§ 371 (c)(1),
(2), (4) Date: Sep. 10, 2008

(87) PCT Pub. No.: WO2007/003784
PCT Pub. Date: Jan. 11, 2007

(65) Prior Publication Data
US 2009/0202465 A1 Aug. 13, 2009

Related U.S. Application Data

(60) Provisional application No. 60/696,789, filed on Jul. 7, 2005.

(30) Foreign Application Priority Data

Jul. 1, 2005 (FR) .................................... 05 52011
Jul. 26, 2005 (FR) .................................... 05 07980

(51) Int. Cl.
| | |
|---|---|
| A61K 8/81 | (2006.01) |
| C08F 120/52 | (2006.01) |
| C08F 26/02 | (2006.01) |
| A61Q 5/00 | (2006.01) |
| C08F 26/06 | (2006.01) |
| A61Q 5/06 | (2006.01) |
| A61Q 1/00 | (2006.01) |
| A61Q 19/00 | (2006.01) |

(52) U.S. Cl.
CPC ............... *A61Q 5/06* (2013.01); *A61K 8/817* (2013.01); *A61K 8/8111* (2013.01); *A61K 8/8158* (2013.01); *A61K 8/8182* (2013.01); *A61Q 1/00* (2013.01); *A61Q 5/00* (2013.01); *A61Q 19/00* (2013.01); *A61K 2800/5426* (2013.01)

(58) Field of Classification Search
None
See application file for complete search history.

(56) References Cited

U.S. PATENT DOCUMENTS

| | | | |
|---|---|---|---|
| 6,300,381 B1 | 10/2001 | Kerres et al. | |
| 2002/0040088 A1 | 4/2002 | Hauschel et al. | |
| 2003/0086895 A1* | 5/2003 | Hanes et al. ................ | 424/70.17 |
| 2004/0142828 A1* | 7/2004 | Popplewell et al. .......... | 510/101 |
| 2006/0188468 A1 | 8/2006 | Nguyen-Kim et al. | |
| 2008/0089853 A1 | 4/2008 | Nguyen-Kim et al. | |

FOREIGN PATENT DOCUMENTS

| | | |
|---|---|---|
| DE | 102004051541 A1 | 5/2006 |
| EP | 1180527 A1 | 2/2002 |
| EP | 1440680 A1 | 7/2004 |
| JP | 09 040996 A | 2/1997 |
| WO | WO-2005004821 A1 | 1/2005 |
| WO | WO-2006045510 A1 | 5/2006 |

OTHER PUBLICATIONS

International Search Report of PCT/FR2006/001547, dated Nov. 16, 2006.
Kim S. J. et al., "Electrical sensitive behavior of a polyelectrolyte complex composed of chitosan/hyaluronic acid," Solid State Ionics, Nov. 2003, pp. 199-204, vol. 164, No. 3-4, North Holland Pub. Company, Amsterdam, NL.
Anonymous, "Structure of Chitin/Chitosan and Cellulose," Dalwoo. com, Apr. 12, 2002, www.dalwoo.com/chitosan/structure.htm.
Lars Keld Nielsen, "Metabolic engineering of hyaluronic acid production," Bioengineering, Jun. 13, 2003, www.cheque.ug.edu.au/research/b1oengineering/research/metabolic_engineering/HA.html.
Derwent abstract for JP 09 040996 A.
Hössel et al., "VP/Methacrylamide/Vinyl Imidazole Copolymer: A New Standard for Hair Styling", SÖFW—Journal, 129th annual series, vol. 12, 2003, pp. 65-70.
IP.com No. IPCOM000097478D (published Mar. 7, 2005).
Opposition dated Aug. 16, 2012 in corresponding Application No. EP 1902077 with English translation.

\* cited by examiner

*Primary Examiner* — Patricia Duffy
*Assistant Examiner* — Garen Gotfredson
(74) *Attorney, Agent, or Firm* — Polsinelli PC

(57) ABSTRACT

The invention relates to an ethylene cationic polymer comprising at least one primary, secondary or tertiary protonable amine function which is at least partially neutralized by a polymer organic acid neutralizing agent which contains at least one carboxylic, sulphonic and/or phosphonic acid function. Said invention also relates to a cosmetic or pharmaceutical composition comprising said neutralized polymer in a physiologically acceptable medium, in particular, cosmetically or pharmaceutically acceptable medium. A method for cosmetically treating keratinic materials, such as a body of face skin, nails, hairs, eyebrows and/or eyelashes, consisting in applying the inventive cosmetic composition to said keratinic materials is also disclosed.

19 Claims, No Drawings

NEUTRALISED CATIONIC POLYMER, COMPOSITION CONTAINING SAID POLYMER AND A COSMETIC TREATMENT METHOD

CROSS REFERENCE TO RELATED APPLICATIONS

This application is a national phase application based on PCT/FR2006/001547, filed Jun. 30, 2006, which claims the priority of French Patent Application Nos. 0552011, filed Jul. 1, 2005; and 0507980, filed Jul. 26, 2005; and claims the benefit of U.S. Provisional Application No. 60/696,789, filed Jul. 7, 2005, the content of all of which is incorporated herein by reference.

The present invention relates to novel polymers, to their use especially in cosmetics, and also to the compositions comprising them.

It is known to employ polymers in the cosmetics field, and especially in the hair field, for example for providing hold or styling to the hair.

In the field of hair compositions referred to as "rinse-out compositions", such as shampoos or conditioners, dyeing or perming compositions, functionalized cationic polymers are used in particular, comprising mainly tertiary or quaternary amine functional groups in hydrochloride, acetate or alkyl sulfonate form, for example. These water-soluble cationic polymers are known for providing a good cosmetic quality to the hair; however, they do not generally provide a hair shaping effect. Furthermore, the cosmetic properties, such as the feel, disentangling or softness, may be improved.

Polymers that provide styling properties with an improved cosmetic quality, in rinse-out mode, are not known.

In the field of hair compositions referred to as "leave-in compositions", such as styling products of the styling spray, gel or lacquer type, there is a continual search for polymers that provide styling effects and hold to the hair, while having an acceptable cosmetic quality: disentangling and feel.

Generally, in hair products, polymers having amine units, such as polymers based on vinylpyrrolidone and on dimethylaminoethyl methacrylate (Gaffix polymers) are known. The compositions obtained have, however, an insufficient hold over time. Polymers of the Luviquat type based on quaternized vinylimidazole and vinylpyrrolidone are also known, which provide softness but thicken the compositions.

In WO 2002/09656, hair compositions are described that comprise hydrophobic polymers based on butyl acrylate, providing a repositionable styling effect.

In EP 1 201 223, hair compositions are described comprising copolymers based on alkyl (meth)acrylates which make it possible to style and restyle the hair at will.

WO 98/30196 describes acrylamide homopolymers having quaternary amines of which the counterions are alkyl sulfate or aryl sulfonate groups.

DE 2446449 describes amine (co)polymer salts comprising hydrophobic comonomers of which the water uptake is less than 20%. Also described are (meth)acrylate polymers having amine units that are neutralized by acetic acid.

JP 09040996 describes the combination of a cationic polymer and a neutralizing anionic polymer chosen from acrylate/acrylamide, vinyl acetate/crotonic acid, vinyl acetate/crotonic acid/vinyl neodecanoate copolymers.

EP 1 038 891 describes the use of a polymer comprising amine groups and a neutralizing divalent or polyvalent acid, and also the use of an acid polymer and a neutralizing amine.

However, in all the documents of the prior art, the cosmetic compositions comprising cationic polymers make it possible to obtain good cosmetic properties, but with inadequate styling effects.

The object of the present invention is therefore to overcome the drawbacks of the prior art and to provide cosmetic compositions comprising cationic polymers, which have a good styling effect while retaining, or even improving, their cosmetic properties, especially the feel, softness, volume and disentangling, whether this be in a dry medium (after drying the hair), or in a wet medium (before drying).

It has been observed that with the compositions according to the invention, the hair shaping and/or manageability effect was particularly improved (gain in styling effect). Furthermore, the compositions according to the invention have a good conditioning effect.

The compositions according to the invention have advantageous cosmetic properties, for example during application in a shampoo type formulation; specifically, it has been observed that the hair is easily disentangled during shampooing, and that they exhibit softness; after drying, the compositions according to the invention also allow, once the hair is dried, a particularly advantageous hair shaping.

One subject of the invention is therefore a cosmetic or pharmaceutical composition comprising, in a physiologically acceptable, especially cosmetically or pharmaceutically acceptable, medium, a cationic ethylenic polymer comprising at least one primary, secondary or tertiary amine functional group that can be protonated, said functional group being at least partially neutralized by a neutralizing agent, characterized in that said neutralizing agent is a polymeric organic acid comprising at least one carboxylic, sulfonic and/or phosphonic acid functional group.

Another subject of the present invention is a cationic ethylenic polymer comprising at least one primary, secondary or tertiary amine functional group that can be protonated, said functional group being at least partially neutralized by a neutralizing agent chosen from polymeric organic acids comprising at least one carboxylic, sulfonic and/or phosphonic acid functional group, said at least partially neutralized polymer being able to be conveyed in an aqueous medium, that is to say being water-soluble or water-dispersible.

Another subject of the invention is a polymer composition comprising such a cationic polymer, comprising at least one primary, secondary or tertiary amine functional group that can be protonated, and (ii) a neutralizing agent, characterized in that said neutralizing agent is a polymeric organic acid comprising at least one carboxylic, sulfonic and/or phosphonic acid functional group.

The present invention has the advantage of providing polymers that can generally be conveyed in water, that is to say that are soluble or dispersible in water, which makes it possible to use them advantageously in cosmetic compositions, especially skincare or hair compositions, generally with an aqueous base.

The expression "water-soluble or soluble in water" is understood to mean that the polymer forms a clear solution in water, in an amount of at least 5% by weight, at 25° C.

The expression "water-dispersible or dispersible in water" is understood to mean that the polymer forms in water, at a concentration of 5% by weight, at 25° C., a stable suspension or dispersion of fine, generally spherical, particles. The average size of the particles forming said dispersion is less than 1 μm and, more generally, varies between 5 and 400 nm, preferably from 10 to 250 nm. These particle sizes are measured by light scattering.

In the remainder of the present description, the expression "cyclic radical" will be understood to mean a monocyclic or polycyclic radical, which may itself be in the form of one or more saturated and/or unsaturated rings which are optionally substituted (for example cyclohexyl, cyclodecyl, benzyl or fluorenyl), but also a radical which comprises one or more of said rings (for example, p-(tert-butyl)cyclohexyl or 4-hydroxybenzyl).

The expression "saturated and/or unsaturated radical" will be understood to mean completely saturated radicals, completely unsaturated radicals, including aromatic radicals, and also radicals comprising one or more double and/or triple bonds, the remainder of the bonds being single bonds.

The cationic polymer according to the invention is an ethylenic polymer comprising at least one amine functional group, which may be primary, secondary or tertiary, said amine functional group having to be able to be protonated at a pH chosen between pH 1 and pH 12.

The expression "able to be protonated" is understood to mean that said amine functional group may be neutralized at least partially by a neutralizing agent according to the invention.

It may of course comprise several primary, secondary and/or tertiary amine functional groups, or a mixture of such functional groups; it may in addition optionally comprise anionic and/or quaternary amine functional groups, and therefore be an amphoteric polymer which will be considered as a cationic polymer in the meaning of the present invention.

The term "ethylenic" polymer is understood to mean, in particular, a polymer obtained by polymerization of monomers comprising an ethylenic unsaturation. It is also understood to mean the polymers obtained by metathesis such as polynorbornen and its derivatives. These polymers may be obtained by radical, anionic or cationic polymerization or by polymerization via transition metal catalysis or via ring opening.

The cationic polymer according to the invention preferably comprises at least one "cationic" monomer of formula (I), of formula (II) and/or of formula (III), which may be present alone or as a mixture.

The monomers of formula (I), likely to be present, alone or as a mixture, in the cationic polymer, are:

(I)

in which:
R$_1$ is a hydrogen atom or a linear or branched, hydrocarbon-based radical of $C_pH_{2p+1}$ type, with p being an integer between 1 and 12 inclusive;
In particular, R$_1$ may represent a methyl, ethyl, propyl or butyl radical. Preferably, R$_1$ represents hydrogen or a methyl radical.
Z is a divalent group chosen from —COO—, —CONH—, —CONCH$_3$—, —OCO— or —O—, —SO$_2$—, —CO—O—CO— or —CO—CH$_2$—CO—;
Preferably Z is chosen from COO and CONH.
x is 0 or 1, preferably 1;
R$_2$ is a saturated or unsaturated, optionally aromatic, linear, branched or cyclic, carbon-based divalent radical having 1 to 30 carbon atoms, which may comprise 1 to 18 heteroatoms chosen from O, N, S, F, Cl, Br, Si and P;

In the R$_2$ radical, the heteroatom or heteroatoms, when they are present, may be inserted into the chain of said R$_2$ radical, or else said R$_2$ radical may be substituted by one or more groups comprising them such as hydroxyl, —CF$_3$, CN, epoxy or amino (NH$_2$, NHR' or NR'R" with R' and R" being identical or different, representing a linear or branched C$_1$-C$_{22}$ alkyl, especially methyl or ethyl).

In particular, R$_2$ may be or may comprise:
an alkylene radical such as methylene, ethylene, propylene, n-butylene, isobutylene, tert-butylene; n-hexylene, n-octylene, n-dodecylene, n-octa-decylene, n-tetradecylene, n-docosanylene;

a phenylene radical (ortho, meta or para) —C$_6$H$_4$— optionally substituted by a C$_1$-C$_{12}$ alkyl radical optionally comprising 1 to 25 heteroatoms chosen from N, O, S, F, Si and/or P; or else a benzylene radical —C$_6$H$_4$—CH$_2$— optionally substituted by a C$_1$-C$_{12}$ alkyl radical optionally comprising 1 to 25 heteroatoms chosen from O, N, S, F, Si and P;

a radical of formula —CO—, —O—CO—O—, —CO—O—, —O—, —O—CO—NH—, —CO—NH—, —NHCO—, —N(R')CO—, —NH—CO—NH—, —NR'—, epoxy, —N—CO— with R' representing a C$_1$-C$_{22}$ linear or branched alkyl radical optionally comprising 1 to 12 heteroatoms chosen from O, N, S, F, Si and P; or a mixture of these radicals;

m is 0 or 1;

X is (a) a guanidino or amidino group, or else;

(b) a group of formula —N(R$_6$)(R$_7$) with R$_6$ and R$_7$ representing, independently of one another, (i) a hydrogen atom, (ii) a linear, branched or cyclic, saturated or unsaturated, optionally aromatic alkyl group comprising from 1 to 18 carbon atoms, which may comprise 1 to 10 heteroatoms chosen from O, N, S, F, Si and P; or (iii) R$_6$ and R$_7$ form, with the nitrogen atom, a ring of formula:

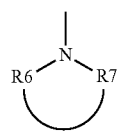

that is saturated or unsaturated, optionally aromatic, comprising in total 5, 6, 7, or 8 atoms, and especially 4, 5 or 6 carbon atoms and/or 2 to 4 heteroatoms chosen from O, S and N; said first ring possibly being fused with one or more other rings, which are saturated or unsaturated, optionally aromatic, each comprising 5, 6 or 7 atoms, and especially 4, 5, 6 or 7 carbon atoms and/or 2 to 4 heteroatoms chosen from O, S and N;

For example, R$_6$ and R$_7$ may be chosen from hydrogen, a methyl, ethyl, propyl, isopropyl, n-butyl, t-butyl, isobutyl, octyl, lauryl or stearyl group.

Preferably, R$_6$ and R$_7$ are chosen, independently of one another, from H, CH$_3$ and C$_2$H$_5$;

or else (c) X may represent a ring:

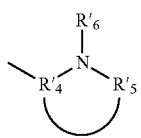

in which R'₄ and R'₅ form, with the nitrogen atom, a saturated or unsaturated, optionally aromatic, ring comprising in total 5, 6, 7 or 8 atoms, and especially 4, 5 or 6 carbon atoms and/or 2 to 4 heteroatoms chosen from O, S and N; said ring possibly being fused with one or more other rings, which are saturated or unsaturated, optionally aromatic, each comprising 5, 6 or 7 atoms, and especially 4, 5, 6, 7 or 8 carbon atoms and/or 2 to 4 heteroatoms chosen from O, S and N; and R'₆ is chosen from H, —CH₃ and —C₂H₅.

For example, X may represent an aromatic or non-aromatic heterocycle containing a secondary or tertiary nitrogen.

Among these preferred X radicals, mention may be made of radicals of the indolyl, isoindolinyl, imidazolyl, imidazolinyl, piperidinyl, pyrazolinyl, pyrazolyl, quinoline, pyridinyl, piperazinyl, pyrrolidinyl, quinidinyl, thiazolinyl, morpholine, guanidine or amidino type, and mixtures thereof.

It is obvious that the monomer of formula (I) must comprise at least one primary, secondary or tertiary amine functional group that can be protonated at a pH chosen between pH 1 and pH 12; this functional group may be, or may be borne by, the $R_2$ radicals and/or X.

Among the preferred monomers of formula (I), mention may be made, alone or as a mixture, of dimethylaminopropyl (meth)acrylamide, dimethylaminoethyl (meth)acrylamide, diethylaminoethyl (meth)acrylate, dimethylaminoethyl (meth)acrylate, tert-butylaminoethyl (meth)acrylate, morpholinoethyl (meth)acrylate, vinylimidazole, vinylpyridine, vinylamine, allylamine, and the monomers below in which R═H or methyl:

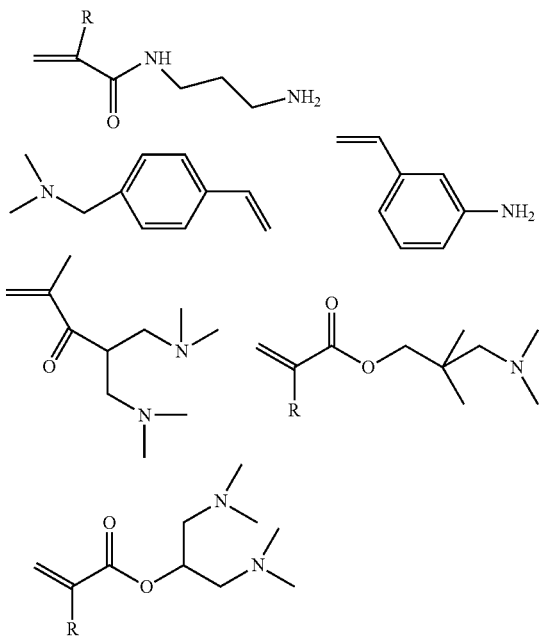

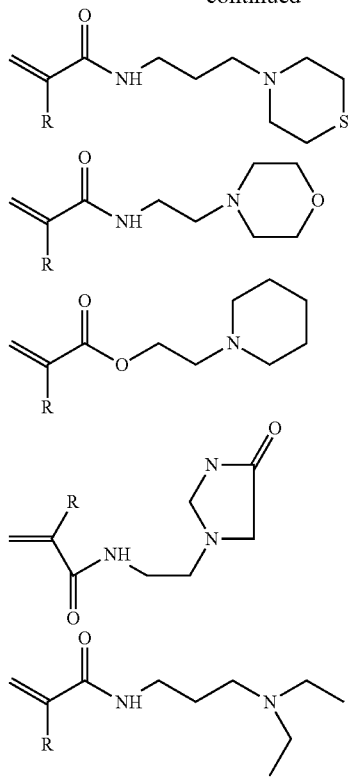

The monomers of formula (II), likely to be present, alone or as a mixture, in the cationic polymer are of the diallyl type as defined below:

(II)

in which $R_3$ is hydrogen or a linear, branched or cyclic, saturated or unsaturated, optionally aromatic, carbon-based, especially hydrocarbon-based, radical having 1 to 30 carbon atoms, which may comprise 1 to 18 heteroatoms chosen from O, N, S, F, Cl, Br, Si and P.

In the $R_3$ radical, the heteroatom or heteroatoms, when they are present, may be inserted into the chain of said $R_3$ radical, or else said $R_3$ radical may be substituted by one or more groups comprising them; in particular, $R_3$ may comprise a group chosen from hydroxyl —OH, CF₃, CN, amino (—NH₂, —NHR' or NR'R" with R' and R", being identical or different, representing a linear or branched $C_1$-$C_{22}$ alkyl, especially methyl or ethyl); —O—CO—O—, —CO—O—, —O—, —O—CO—NH—, —NH—CO—NH—, —CO—NH—, —NR'—, —N—CO— with R' representing a linear or branched $C_1$-$C_{22}$ alkyl optionally comprising 1 to 12 heteroatoms chosen from O, N, S, F, Si and P.

In particular, $R_3$ may be:
an alkyl radical such as methyl, ethyl, propyl, n-butyl, isobutyl, tert-butyl, n-hexyl, n-octyl, n-dodecyl, n-octadecyl, n-tetradecyl, n-docosanyl; optionally comprising 1 to 25 heteroatoms chosen from O, N, S, F, Si and P and/or optionally substituted by at least one of the aforementioned groups;

a phenyl radical —$C_6H_5$ optionally substituted by a $C_1$-$C_{12}$ alkyl radical optionally comprising 1 to 25 heteroatoms chosen from N, O, S, F, Cl, Br, Si and/or P; and/or optionally substituted by at least one of the aforementioned groups;

a benzyl radical —$C_6H_4$—$CH_3$ optionally substituted by a $C_1$-$C_{12}$ alkyl radical optionally comprising 1 to 25 heteroatoms chosen from O, N, S, F, Cl, Br, Si and P; and/or optionally substituted by at least one of the aforementioned groups; or a mixture of these radicals.

It is obvious that the monomer of formula (II) must comprise at least one primary, secondary or tertiary amine functional group that can be protonated at a pH chosen between pH 1 and pH 12.

Preferably, $R_3$ is H or methyl.

Among the monomers of formula (II), mention may especially be made of N-methyldiallylamine ($R_3$=methyl) and diallylamine ($R_3$=H)

The monomers of formula (III), likely to be present, alone or as a mixture, in the cationic polymer, are:

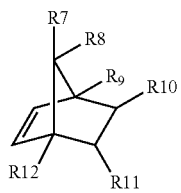

(III)

in which $R_7$ to $R_{12}$, independently of one another, represent:

a hydrogen atom;

an —$NR_{13}R'_{13}$ group with $R_{13}$ and $R'_{13}$, independently of one another, representing hydrogen or a linear, branched or cyclic, saturated or unsaturated, optionally aromatic alkyl comprising from 1 to 18 carbon atoms, which may comprise 1 to 10 heteroatoms chosen from O, N, S, F, Si and P; and in particular $R_{13}$ and $R'_{13}$ may be chosen from hydrogen, a methyl, ethyl, propyl, isopropyl, n-butyl, t-butyl, isobutyl, octyl, lauryl or stearyl group.

Preferably, —$NR_{13}R'_{13}$ represents —$NH_2$, —$N(CH_3)_2$, —$N(C_2H_5)_2$, —$N(isopropyl)_2$ or —$N(butyl)_2$.

a linear, branched or cyclic, saturated or unsaturated, optionally aromatic, carbon-based, especially hydrocarbon-based, radical having 1 to 30 carbon atoms, possibly comprising 1 to 18 heteroatoms chosen from O, N, S, F, Si and P.

In these radicals, the heteroatom or heteroatoms, when they are present, may be inserted into the chain of the radical, or else the radical may be substituted by one or more groups comprising them; in particular, the radical may comprise a group chosen from hydroxyl —OH, $CF_3$, CN, epoxy, amino (—$NH_2$, —NHR' or —NR'R" with R' and R", being identical or different, representing a linear or branched $C_1$-$C_{22}$ alkyl, especially methyl or ethyl); —C(O)—, —O—CO—O—, —CO—O—, —O—, —O—CO—NH—, —NH—CO—NH—, —CO—NH—, —NHCO—, N(R') CO—, —NR'—, —N—CO— with R' representing a linear or branched $C_1$-$C_{22}$ alkyl optionally comprising 1 to 12 heteroatoms chosen from O, N, S, F, Si and P.

It is obvious that the monomer of formula (III) must comprise at least one primary, secondary or tertiary amine functional group that can be protonated at a pH chosen between pH 1 and pH 12.

In particular, $R_7$ to $R_{12}$ may be:

H;

$NH_2$;

an alkyl radical such as methyl, ethyl, propyl, n-butyl, isobutyl, tert-butyl, n-hexyl, n-octyl, n-dodecyl, n-octadecyl, n-tetradecyl, n-docosanyl; optionally comprising 1 to 25 heteroatoms chosen from O, N, S, F, Si and P and/or optionally substituted by at least one of the aforementioned groups;

a phenyl radical —$C_6H_5$ optionally substituted by a $C_1$-$C_{12}$ alkyl radical optionally comprising 1 to 25 heteroatoms chosen from N, O, S, F, Si and/or P; and/or optionally substituted by at least one of the aforementioned groups;

a benzyl radical —$C_6H_4$—$CH_3$ optionally substituted by a $C_1$-$C_{12}$ alkyl radical optionally comprising 1 to 25 heteroatoms chosen from O, N, S, F, Si and P; and/or optionally substituted by at least one of the aforementioned groups; or a mixture of these radicals.

Preferably, at least one of the radicals $R_7$ to $R_{12}$ is of the form —$NR_{13}R'_{13}$, very preferably, it is the $R_{11}$ radical.

Preferably, $R_{11}$=$NH_2$.

Preferably, $R_7$=H or methyl.

Preferably, $R_8$=H or methyl.

Preferably, $R_9$=H or methyl.

Preferably, $R_{10}$=$CH_2OH$ or —C(O)OEt.

Preferably, $R_{12}$=H or methyl.

Among the monomers of formula (III), mention may especially be made of the following monomers:

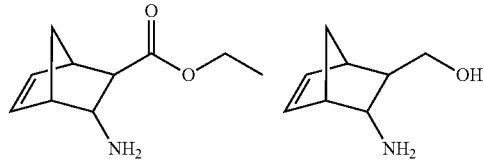

The monomers of formula (I), (II) and/or (III) may represent all of the monomers present in the polymer (i.e. 100% by weight relative to the weight of the final polymer), or else may be present in an amount of 1 to 99.9% by weight relative to the weight of the final polymer, especially 30 to 95% by weight, preferably 35 to 90% by weight, or even in an amount of 40 to 85% by weight.

It is therefore possible that, optionally, the cationic polymer according to the invention comprises additional, non-cationic monomers which may be present in an amount of 0.01 to 99% by weight relative to the weight of the final polymer, especially from 5 to 70% by weight, preferably from 10 to 65% by weight, or even in an amount of 15 to 60% by weight.

These additional monomers may be chosen from the following monomers, alone or as a mixture, and also their salts:

(i) (meth)acrylic acid esters of formula $CH_2$=CHCOOR'1 or $CH_2$=C($CH_3$)COOR'1 with $R'_1$ representing a linear, branched or cyclic, saturated or unsaturated, optionally aromatic (aryl, aralkyl or alkylaryl) carbon-based, especially hydrocarbon-based (alkyl), chain having 1 to 30 carbon atoms, optionally comprising 0 to 2 ether functional groups (—O—) and optionally 0 to 12, especially 1 to 8, functional groups chosen from —OH (hydroxyl), —OR' with R' a $C_1$-$C_6$ alkyl (alkoxy), —CN, —X (halogen, especially Cl, F, Br or I), —CO—, —SO$_3$H, —COOH, —OCOO—, —COO—, —OCONR—, —OCONH—, —NH—CONH—, —NR—CONR—, —CF$_3$, —CN, epoxy, —NHCO—, —N(R)CO— with R=linear or branched C$_1$-C$_{22}$ alkyl optionally comprising 1-12 heteroatoms;

Thus, mention may be made of methyl, ethyl, propyl, isopropyl, n-butyl, isobutyl, tert-butyl, hexyl, cyclohexyl, 2-ethylhexyl, octyl, isooctyl, isodecyl, decyl, dodecyl, myristyl, cetyl, palmityl, stearyl, behenyl, oleyl, tridecyl, hexadecyl, isobornyl, hydroxyethyl, hydroxypropyl, phenyl, benzyl, furfuryl; tetrahydrofurfuryl, ethoxyethyl, methoxyethyl; glycerol, 2,2,2,-trifluoroethyl and poly(ethylene-isobutylene) (meth)acrylates; (meth)acrylonitriles.

(ii) (meth)acrylic acid amides of formula CH$_2$=CHCONR'$_2$R"$_2$ or CH$_2$=C(CH$_3$)CONR'$_2$R"$_2$, with R'$_2$, R"$_2$, being identical or different, representing hydrogen or a linear, branched or cyclic, saturated or unsaturated, optionally aromatic, carbon-based, especially hydrocarbon-based (alkyl), chain having 1 to 30 carbon atoms, optionally comprising 0 to 2 ether functional groups (—O—) and optionally 0 to 12, especially 1 to 8, functional groups chosen from —OH (hydroxyl), —OR' with R' a C$_1$-C$_6$ alkyl (alkoxy), —CN, —X (halogen, especially Cl, F, Br or I), —CO—, —SO$_3$H, —COOH, —OCOO—, —COO—, —OCONR—, —OCONH—, —NH—CONH—, —NR—CONR—, —CF$_3$, —CN, epoxy, —NHCO—, —N(R)CO— with R=linear or branched C$_1$-C$_{22}$ alkyl optionally comprising 1-12 heteroatoms.

Thus, mention may be made of (meth)acrylamide, N-methyl(meth)acrylamide, N-isopropyl(meth)acrylamide, N-tert-butyl(meth)acrylamide, N-octyl(meth)acrylamide, N-undecyl(meth)acrylamide, N,N-dimethyl(meth)acrylamide, N,N-dibutyl(meth)acrylamide;

(iii) vinyl esters of formula CH$_2$=CH—OCO—R'$_3$ or CH$_2$=C(CH$_3$)—OCO—R'$_3$ with R'$_3$ representing a linear, branched or cyclic, saturated or unsaturated, optionally aromatic, carbon-based, especially hydrocarbon-based, chain having 1 to 30 carbon atoms, optionally comprising 0 to 2 ether functional groups (—O—) and optionally 0 to 12, especially 1 to 8, functional groups chosen from —OH (hydroxyl), —OR' with R' a C$_1$-C$_6$ alkyl (alkoxy), —CN, —X (halogen, especially Cl, F, Br or I), —CO—, —SO$_3$H, —COOH, —OCOO—, —COO—, —OCONR—, —OCONH—, —NH—CONH—, —NR—CONR—, —CF$_3$, —CN, epoxy, —NHCO—, —N(R)CO— with R=linear or branched C$_1$-C$_{22}$ alkyl optionally comprising 1-12 heteroatoms;

Mention may especially be made of vinyl acetate, vinyl propionate, vinyl butyrate (or butanoate), vinyl ethylhexanoate, vinyl neononanoate and vinyl neododecanoate, vinyl neodecanoate, vinyl pivalate, vinyl cyclohexanoate, vinyl benzoate, vinyl 4-tert-butylbenzoate, vinyl trifluoroacetate;

(iv) vinyl ethers of formula CH$_2$=CHOR'$_4$ or CH$_2$=C(CH$_3$)OR'$_4$ with R'$_4$ representing a linear, branched or cyclic, saturated or unsaturated, optionally aromatic, carbon-based, especially hydrocarbon-based, chain having 1 to 30 carbon atoms, optionally comprising 0 to 2 ether functional groups (—O—) and optionally 0 to 12, especially 1 to 8 functional groups chosen from —OH (hydroxyl), —OR' with R' a C$_1$-C$_6$ alkyl (alkoxy), —CN, —X (halogen, especially Cl, F, Br or I), —CO—, —SO$_3$H, —COOH, —OCOO—, —COO—, —OCONR—, —OCONH—, —NH—CONH—, —NR—CONR—, —CF$_3$, —CN, epoxy, —NHCO—, —N(R)CO— with R=linear or branched C$_1$-C$_{22}$ alkyl optionally comprising 1-12 heteroatoms.

Mention may be made of methyl vinyl ether, ethyl vinyl ether, ethylhexyl vinyl ether and butyl vinyl ether, cyclohexyl vinyl ether, isobutyl vinyl ether;

(v) vinyl compounds of formula CHR"$_5$=CR$_5$R'$_5$ in which:

R"$_5$ is H or COOH, and

R$_5$ is H, CN or COOH, and

R'$_5$ is chosen from:

a hydrogen atom, or a group chosen from —OH, —CH=O, halogen (Cl, Br, I in particular), —COOH, —CH$_2$COOH, —NHC(O)H, —N(CH$_3$)—C(O)H, —NHC(O)CH$_3$, —N(CH$_3$)—C(O)CH$_3$;

a ring:

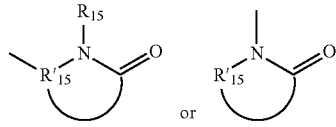

where R'$_{15}$ and R$_{15}$ represent, independently of one another, H, a linear or branched, saturated or unsaturated, optionally aromatic, cyclic or non-cyclic alkyl group, comprising 1 to 25 carbon atoms, optionally inserted into which are one, or more heteroatoms chosen from O, N, S and P; said alkyl group possibly, moreover, being optionally substituted by one or more substituents chosen from —OH and halogen atoms (Cl, Br, I and F);

a linear or branched alkyl group comprising 1 to 25 carbon atoms;

a C$_3$ to C$_8$ cycloalkyl group such as cyclohexane;

a C$_6$ to C$_{20}$ aryl group such as phenyl;

a C$_7$ to C$_{30}$ aralkyl group (C$_1$ to C$_4$ alkyl group) such as 2-phenylethyl or benzyl;

a heterocyclic group having 4 to 12 chain members containing one or more heteroatoms chosen from O, N and S; and a heterocycloalkyl group (alkyl having 1 to 4 carbons), such as furfuryl, furfurylmethyl or tetrahydrofurfurylmethyl, said alkyl, cycloalkyl, aryl, aralkyl, heterocyclic or heterocycloalkyl groups possibly optionally comprising 0 to 2 ether functional groups (—O—) and optionally 0 to 12, especially 1 to 8, functional groups chosen from —OH (hydroxyl), —OR' with R' a C$_1$-C$_6$ alkyl (alkoxy), —CN, —X (halogen, especially Cl, F, Br or I), —CO—, —SO$_3$H, —COOH, —OCOO—, —COO—, —OCONR—, —OCONH—, —NH—CONH—, —NR—CONR—, —CF$_3$, —CN, epoxy, —NHCO—, —N(R)CO— with R=linear or branched C$_1$-C$_{22}$ alkyl optionally comprising 1-12 heteroatoms;

and/or possibly being optionally substituted by one or more linear or branched, C$_1$-C$_4$ alkyl groups, themselves optionally comprising 0 to 2 ether functional groups (—O—) and optionally 0 to 12, especially 1 to 8, functional groups chosen from —OH (hydroxyl), —OR' with R' a C$_1$-C$_6$ alkyl (alkoxy), —CN, —X (halogen, especially Cl, F, Br or I), —CO—, —SO$_3$H, —COOH, —OCOO—, —COO—, —OCONH—, —NH—CONH—, —CF$_3$, —CN, epoxy, —NHCO—, —N(R)CO— with R=linear or branched C$_1$-C$_{22}$ alkyl optionally comprising 1-12 heteroatoms.

Examples of such vinyl monomers are vinyl alcohol, vinylcyclohexane; vinylpyrrolidone, vinylcaprolactam, N-vinylacetamide, N-vinylformamide, N-methyl-N-vinylformamide, N-vinylacetamide; N-methyl-N-vinylacetamide; styrene, methylstyrene, 4-tert-butylstyrene, 4-acetoxy-styrene, 4-methoxystyrene, 3-methylstyrene, 4-methylstyrene, 2-chlorostyrene, 3-chlorostyrene, 4-chlorostyrene, dimethylstyrene, 2,6-dichlorostyrene, 2,4-dimethylstyrene; 2,5-dimethylstyrene, 3,5-ethoxystyrene, 2,4-ethoxystyrene, 4-fluorostyrene; vinyl butyral; vinylcarbazole; vinylchloride; vinyl formal; vinylidene chloride, vinylidene fluoride, 2-vinylnaphthalene; N-methylmaleimide; 1-octene, 1-butene, cis-chlorobutadiene, trans-chlorobutadiene, chlorotrifluoroethylene; cis-isoprene, trans-isoprene, 1-octadecene, butadiene, hexadecane and eicosene.

(vii) the following anionic monomers, and salts thereof: maleic anhydride, acrylic acid, methacrylic acid, crotonic acid, itaconic acid, fumaric acid, maleic acid, 2-carboxyethyl acrylate ($CH_2=CH-C(O)-O-(CH_2)_2-COOH$), styrenesulfonic acid, 2-acrylamido-2-methylpropanesulfonic acid, vinylbenzoic acid, vinylphosphonic acid, sulfopropyl (meth)acrylate, and among the salts: sodium or potassium (meth)acrylate;

(viii) the following amphoteric monomers: N,N-dimethyl-N-(2-methacryloyloxyethyl)-N-(3-sulfopropyl) ammonium betaine (especially SPE from Raschig); N,N-dimethyl-N-(3-methacrylamidopropyl)-N-(3-sulfopropyl)ammonium betaine (SPP from Raschig), and 1-(3-sulfopropyl)-2-vinylpyridinium betaine (SPV from Raschig), and also 2-(methacryloyloxy)ethyl phosphorylcholine;

(ix) monomers of formula:

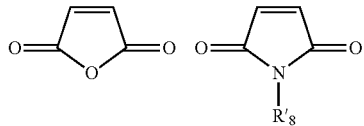

in which $R'_8$ is H or a linear or branched, saturated or unsaturated, optionally aromatic, cyclic or non-cyclic alkyl group comprising 1 to 25 carbon atoms, optionally inserted into which are one or more heteroatoms chosen from O, N, S and P; said alkyl group possibly, moreover, being optionally substituted by one or more substituents chosen from —OH and halogen atoms (Cl, Br, I and F);

Mention may especially be made of maleic anhydride and N-methyl maleimide.

(x) quaternized monomers of formula (I), (II) and (III), and the quaternized forms of the additional monomers above.

Mention may especially be made of N,N'-dimethyldiallylammonium chloride; triethylammonium ethyl methacrylate chloride (MADQUAT), 4-methylvinyl-pyridinium chloride, N-methyl-N-vinylimidazolinium chloride, trimethylammonium propyl (meth)acrylamide chloride.

(xi) multivalent compounds comprising at least two polymerizable functional groups of the vinyl, (meth)acrylic, allyl or (meth)acrylamide type, and especially difunctional monomers such as 1,3-butanediol di(meth)acrylate; 1,6-hexanediol di(meth)acrylate and N,N'-dimethyldiallylammonium chloride.

Among the preferred additional monomers, mention may be made of those chosen from vinyl neodecanoate, vinyl tert-butylbenzoate; vinylpyrrolidone; vinylcaprolactam; N-vinylformamide; N,N'-dimethyldiallylammonium chloride; triethylammonium ethylmethacrylate chloride (MADQUAT); ethyl, methyl, tert-butyl or isobornyl (meth)acrylate; vinyl acetate, crotonic acid; (meth)acrylic acid, methacryloyl ethyl betaine, octylacrylamide; N-methyl-N-vinylimidazolinium chloride, 1-eicosene, tert-butylacrylamide, acrylamide, hexadecene, and mixtures thereof.

The cationic polymer according to the invention comprises at least three repeating units; it may be in the form of a homopolymer or a copolymer which may be linear or branched, crosslinked or uncrosslinked; it may be a random, alternating, block or gradient, or even star homopolymer or copolymer. It is preferably a linear, random or block homopolymer or copolymer.

In one particular embodiment of the invention, the cationic polymer according to the invention does not comprise a monomer of formula (I'):

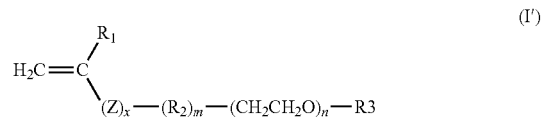

in which:
$R_1$ is a hydrogen atom or a linear or branched, hydrocarbon-based radical of $C_pH_{2p+1}$ type, with p being an integer between 1 and 12 inclusive;
Z is a divalent group chosen from —COO—, —CONH—, —CONCH$_3$—, —OCO—, —O—, —SO$_2$—, —CO—O—CO— or —CO—CH$_2$—CO—;
x is 0 or 1;
$R_2$ is a saturated or unsaturated, optionally aromatic, linear, branched or cyclic, carbon-based divalent radical having 1 to 30 carbon atoms, which may comprise 1 to 18 heteroatoms chosen from O, N, S, F, Si and P;
m is 0 or 1;
n is an integer between 3 and 300 inclusive; and
$R_3$ is a hydrogen atom or a linear, branched or cyclic, saturated or unsaturated, optionally aromatic carbon-based radical having 1 to 30 carbon atoms, which may comprise 1 to 20 heteroatoms chosen from O, N, S, F, Si and P;
and salts thereof.

Mention may especially be made, among the preferred polymers according to the invention, of:
poly(vinylpyrrolidone-co-dimethylaminoethyl methacrylate) copolymers, especially those known under the trade name Copolymer 845, 937 and 958 supplied by ISP;
poly(vinylcaprolactam-co-vinylpyrrolidone-co-dimethylaminoethyl methacrylate) copolymers, especially those sold under the trade name Gaffix VC 713 or H20LD from ISP;
poly(vinylpyrrolidone-co-dimethylaminopropyl methacrylamide) copolymers, especially that sold under the name Styleze CC-10 from ISP;
poly(vinylpyrrolidone-co-polyvinylcaprolactam-co-dimethylaminopropyl methacrylamide) copolymers, especially Aquaflex SF-40 from ISP;
poly(vinylamine), poly(allylamine), poly(diallylamine); and
poly(N-vinylformamide-co-vinylamine) copolymers.

The polymers according to the invention have a weight-average molecular weight ($M_w$) which is preferably between 1000 and 3,000,000, especially between 1500 and 1,000,000 and more preferably between 2000 and 800,000, and even better between 2500 and 500,000. The weight-average molecular weights ($M_w$) are determined by gel permeation chromatography or by light scattering, depending on the accessibility of the method (solubility of the polymers in question).

These polymers may optionally be functionalized so as to give them a soluble or dispersible nature, especially in the solvent in which they are intended to be formulated, such as for example water, alcohols and especially ethanol, or else carbon-based, ester, fluoro or silicone oils and/or mixtures thereof.

The polymers according to the invention may be prepared according to the usual methods of conventional radical polymerization, well known to a person skilled in the art and as described, for example, in the work "Chimie et physico-chimie des polymères" (Chemistry and Physical Chemistry of Polymers) by Gnanou et al. (Dunod Publishers).

In particular, these polymers may be prepared by:
direct polymerization in solution in water with or without pre-neutralization of the cationic unit and/or of the anionic unit;
emulsion polymerization in water with or without pre-neutralization of the cationic unit and/or of the anionic unit, with use of a surfactant; and
polymerization in an organic solvent, such as ethanol or methyl ethyl ketone, with or without pre-neutralization of the cationic unit and/or of the anionic unit, followed by a step of dissolving or dispersing in water with evaporation of the solvent.

These polymerizations may be carried out in the presence of a radical initiator especially of the peroxide type (Trigonox 21S: tert-butylperoxy 2-ethylhexanoate) or azo type (AIBN or V50: 2,2'-azobis(2-amidinopropane)dihydrochloride) or potassium or ammonium persulfate, which may be present in an amount of 0.1 to 5% by weight relative to the total weight of the monomers.

According to a first embodiment, the cationic polymer may be prepared by polymerization via a common, especially radical, anionic, coordination (transition metal catalysis), cationic, or ring-opening mechanism, of at least one monomer comprising at least one amine functional group that can be protonated, and optionally of one or more additional comonomers. In this case, the amine functional group that can be protonated results from the copolymerization of a monomer bearing it.

According to a second embodiment, the cationic polymer according to the invention may be prepared by polymerization, via a common mechanism, of at least one monomer bearing a protected amine functional group (precursor of amine functional groups) and optionally of one or more additional comonomers. In this case, the amine functional group that can be protonated then results from a conversion step subsequent to the polymerization.

These precursor monomers may comprise:
at least one ethylenic unit of the type: (meth)acrylic, (meth)acrylamide, vinyl, allyl, cyclic or non-cyclic ethylenic such as dienes, norbornenes and derivatives, diallylamines and derivatives or mixtures thereof capable of polymerizing via radical, anionic or cationic polymerization by ring opening.

This precursor monomer may also comprise a heterocycle of the oxazoline type; and
at least one site capable of generating, in a step subsequent to the polymerization, a primary, secondary or tertiary amine functional group.

Thus, mention may be made, as a precursor monomer, of N-vinylformamide which results, after polymerization, in poly(N-vinylformamide), then, via basic hydrolysis, in poly(vinylamine) when the hydrolysis is complete, or in a poly(vinylformamide-co-vinylamine) copolymer in the case of a partial hydrolysis.

It may also be BOC-3-exo-hydroxymethyl-bicyclo[2.2.1]hept-5-enyl-2-exo-amine which after deprotection of the BOC protecting functional group results in the production of a polymer comprising an amine functional group that can be protonated:

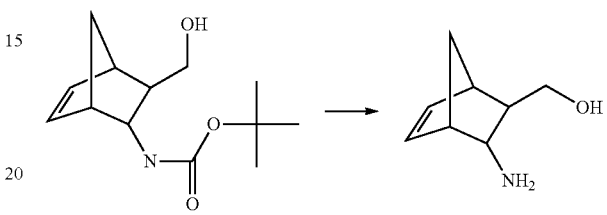

Mention may also be made of ethyloxazoline which, after polymerization and acid hydrolysis may result in a linear polyethyleneimine:

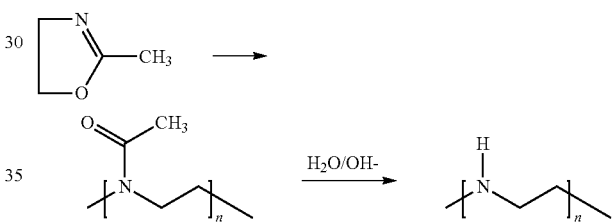

Mention may further be made of the opening of aziridine which results in a branched polyethyleneimine:

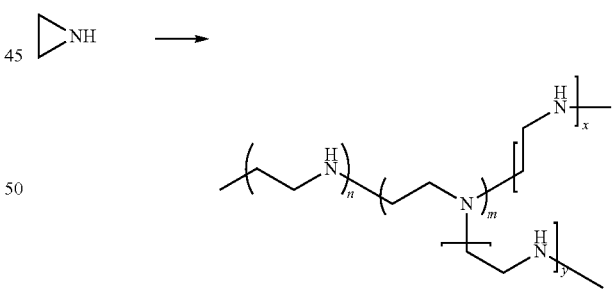

It may also be a monomer such as 1,3-diacetyl-1,3-dihydro-2H-imidazol-2-one which, via polymerization then basic hydrolysis, results in the production of polymethyleneimine:

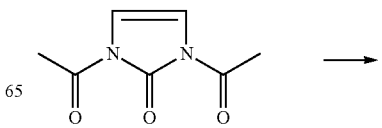

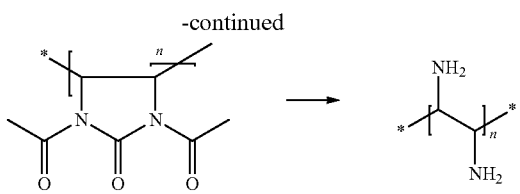

Thus, the cationic polymer according to the invention may also comprise repeating units chosen, alone or as mixtures, from:

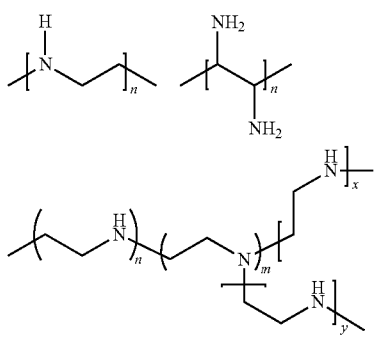

The polymer according to the invention is, when it is ready to be used for preparing compositions according to the invention, for example in a state that is neutralized (its amine units are neutralized) by at least one particular neutralizing agent chosen from polymeric organic acids, comprising at least one Brønsted-type acid functional group.

This is understood to mean that the monomers, especially those of formula (I) and/or the final polymer, have been neutralized by at least one such neutralizing agent.

It is thus possible to neutralize the primary, secondary and/or tertiary amine units, of the monomers of formula (I), (II) or (III), incorporated in the composition of the polymer, before their polymerization, then to copolymerize all the monomers in order to obtain the polymer according to the invention; this is then referred to as pre-neutralization.

It is also possible to first polymerize all the monomers, then neutralize the polymer after it has been formed. This is referred to as neutralization or post-neutralization.

Preferably, the polymer is neutralized after it has been formed.

The term "neutralization" is understood according to the invention to mean the action of an organic acid according to the invention, comprising at least one Brønsted-type acid functional group, over all or some of the monomers and/or polymer mentioned above, comprising at least one Brønsted-type basic functional group (amine units).

The neutralizing agent may be added in an amount of 0.01 to 3 molar equivalents, especially 0.05 to 2.5, or even 0.1 to 2 molar equivalents, relative to the total amine functional groups of the polymer or of the monomers.

It is thus possible to partially neutralize the polymer, that is to say that the neutralizing agent may be present in an amount required to neutralize 1 to 99%, especially 5 to 90%, or even 10 to 80%, of the total amine functional groups of the polymer or of the monomers; which means that it is present in an amount of 0.01 to 0.99 molar equivalents, especially 0.05 to 0.9, or even 0.1 to 0.8 molar equivalents.

It is also possible to over-neutralize the polymer, that is to say that the neutralizing agent may be present in excess, in an amount required to neutralize 101 to 300%, especially 120 to 250%, or even 150 to 200%, of the total amine functional groups of the polymer or of the monomers; this may be the case when it is desired to ensure that the polymer has a pH range and/or an ionic strength that are adequate with respect to the envisaged formulations. It may therefore be present in an amount of 1.01 to 3 molar equivalents, especially 1.2 to 2.5, or even 1.5 to 2 molar equivalents, relative to the total amine functional groups of the polymer or of the monomers.

Preferably, the neutralizing agent is present in a stoichiometric amount relative to the total amine functional groups of the polymer or of the monomers; it is therefore present in an amount required to neutralize 100% of the amine units of the polymer or of the monomers, i.e. 1 molar equivalent.

It is obviously possible to use a mixture of neutralizing agents according to the invention.

Furthermore, when the polymer is partially neutralized by one neutralizing agent according to the invention, it is possible to moreover add a second neutralizing agent, chosen from mineral acids, and especially hydrochloric acid, sulfuric acid, and/or non-polymeric organic acids, such as tartaric acid, gluconic acid, lactic acid, benzoic acid or acetic acid.

Preferably, the nature and the amount of neutralizing agent may be determined by a person skilled in the art so as to obtain at the end a polymer which is soluble or dispersible in water.

The neutralizing agent according to the invention is polymeric; this is understood to mean that it is a polymer, homopolymer or copolymer, comprising at least 3 repeating units.

In one particular embodiment, the neutralizing agent is a polymer which comprises at least three repeating units of the alkylene glycol type, preferably of the ethylene glycol type; ($—CH_2—CH_2—O—$).

The polymeric neutralizing agent may especially have a linear, branched, graft, block (diblock, triblock, multiblock), star-shaped or dendrimer type structure. It may be random, alternating or gradient.

Linear, random or block polymeric neutralizing agents are preferred.

It preferably has a number-average molecular weight ($M_n$) between 300 and 50,000, especially between 350 and 20,000, and more preferably between 400 and 10,000, or even 450 and 5000 (g/mol).

The neutralizing agent therefore comprises at least one Brønsted-type acid functional group, and especially 1 to 6 acid functional groups, or even 2 to 5 acid functional groups, chosen from the carboxylic ($—COOH$), sulfonic ($—SO_3H$) and/or phosphonic ($—PO_3H_2$) acid groups; said groups being capable of protonating, completely or partially, the primary, secondary and/or tertiary amine functional groups of the cationic polymer.

The acid functional group or groups may be located at the chain ends (at the extremities) and/or be distributed along the chain.

Preferably, at least one acid functional group is a chain end; when there are two acid functional groups, they are preferably each at one end of the chain.

When the neutralizing agent is linear, it preferably comprises 1 to 3 acid functional groups, of which preferably at least one of them is at the chain end.

When the neutralizing agent has a graft, branched, star-shaped or dendrimer type structure, it preferably comprises 1 to 6 acid functional groups, preferably distributed so as to have one functional group per branch.

Preferably, the neutralizing agent is linear and comprises two acid functional groups, one at each end of the chain.

According to another embodiment, the neutralizing agent is linear and comprises a single terminal acid functional group at one of the chain ends.

According to yet another embodiment, the neutralizing agent is branched and the acid functional groups are distributed at the chain ends.

The neutralizing agent according to the invention is preferably chosen from hydrophilic polymeric organic acids, that is to say that it is preferably composed solely (100%) or at least 80% by weight, of hydrophilic repeating units.

The term "hydrophilic" is understood to mean that the repeating units have a log P less than or equal to 0.5, preferably between −8 and 0.5; especially between −6 and 0.

Preferably, the neutralizing agent is soluble in water, at 25° C., in an amount of at least 5% by weight.

The log P values are known and are determined according to a standard test which determines the concentration of the compound in 1-octanol and water.

The values may especially be calculated using the ACD (Advanced Chemistry Development) software solaris V4.67; they may also be obtained from Exploring QSAR: hydrophobic, electronic and steric constants (ACS professional reference book, 1995). There is also an Internet site which supplies estimated values (address: http://esc.syrres.com/interkow/kowdemo.htm).

Given below are the log P values of certain well-known units, capable of forming all or part of the neutralizing agent.

| UNIT | LOG P FRAGMENT VALUE |
| --- | --- |
| —CH2—O— | −0.246 |
| —CH2—CH2—O— | −0.136 |
| —CH2—CH—OH | −0.493 |
| —CH2—CH(OCH3)— | 0.295 |
| —CH2—CH2—CH(CH3)—O | 0.684 |
| —CH2—CH2—CH2—CH2—O— | 0.176 |
| —CH2(OH)—CH(OH)—CH2(OH)— | −2.476 |
| —N—(COC2H5)—CH2—CH2 | 1.016 |
| 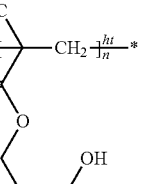 | −0.7038 |
| 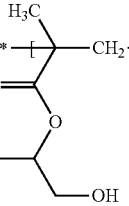 | −0.7532 |
| 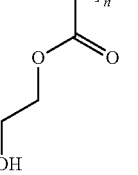 | 0.1214 |
| 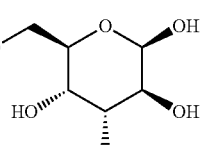 | −2.21345 |
| 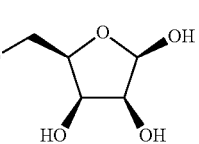 | −2.064 |
| 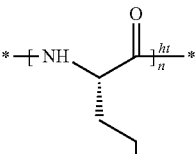 Glu | −1.1456 |

Mention may also be made of sarcosine and methyloxazoline.

The neutralizing agent may however comprise hydrophobic repeating units, that is to say having a log P greater than 0.5, but preferably in a ratio (number of hydrophilic units)/(number of hydrophobic units) greater than 5, preferably greater than 10.

Preferably, the neutralizing agent only comprises hydrophilic sequences, which are terminated at both or at one end by an acid functional group.

The neutralizing agent may be chosen from:
(i) polymers consisting of dextran repeating units comprising at least one acid, especially carboxylic acid, functional group as a chain end;
(ii) acid-terminated poly(alkyloxazolines), preferably poly(methyloxazoline) and poly(ethyloxazoline) comprising at least one acid functional group;
(iii) acid, especially carboxylic acid, functionalized poly (N-methylsarcosines);
(iv) dendrimers or hyperbranched molecules that are functionalized at the surface with acid, especially carboxylic acid, groups; such as for example the starburst PAMAM dendrimers from Dow Chemical;
(v) hyperbranched polymers of the polyester type obtained by reaction between adipic acid and glycerol;
(vi) acid, especially carboxylic acid, terminated poly (glycerol), poly(hydroxyethyl acrylate) and poly(vinylpyrrolidone);

However, the neutralizing agent according to the invention is preferably chosen from:
(vii) polymers comprising at least three alkylene glycol type repeating units for which the alkyl group comprises 2 to 4 carbon atoms, and combinations thereof; mention may be made of polyethylene glycol, polypropylene glycol, polyethylene-co-propylene glycol (PEG/PPO), polytetramethylene oxide-co-polyethylene glycol (PTMO/PEG); being understood that they furthermore comprise at least one acid (especially carboxylic, sulfonic and/or phosphonic acid) functional group.

They may be random, block, branched or star polymers or homopolymers; they may comprise other repeating units, for example of the siloxane type, especially PDMS. Preferably, the neutralizing agent is chosen from homopolymers of polyalkylene glycols ($C_2$-$C_3$ alkyl), or random or block copolymers of polyalkylene glycols ($C_2$-$C_3$ alkyl). Mention may be made, in particular, of polymers having the following structures:

$CH_3$—O—($CH_2$—$CH_2$—O—)—CO—($CH_2$—CHR—O)$_m$—$CH_2$—$R_{10}$
$CH_3$—O—($CH_2$—$CH_2$—O—)$_n$-b-($CH_2$—CHR—O)$_m$—$CH_2$—$R_{10}$
$CH_3$—O—($CH_2$—$CH_2$—O—)$_n$-co-($CH_2$—CHR—O)$_m$—$CH_2$—$CH_2$ $R_{10}$
$CH_3$—O—($CH_2$—$CH_2$—O—)$_n$-b-($CH_2$—CHR—O)$_m$—$CH_2$—$CH_2$ $R_{10}$
$CH_3$—O—($CH_2$—$CH_2$—O—)$_n$-co-($CH_2$—CHR—O)$_m$—$CH_2$—$CH_2CH_2$ $R_{10}$
$CH_3$—O—($CH_2$—$CH_2$—O—)$_n$-b-($CH_2$—CHR—O)$_m$—$CH_2$—$CH_2CH_2$ $R_{10}$
$CH_3$—O—($CH_2$—$CH_2$—O—)$_n$-co-($CH_2$—CHR—O)$_m$—$CH_2CH_2$OCO—$CH_2$—$CH_2$—COOH
$CH_3$—O—($CH_2$—$CH_2$—O—)$_n$-b-($CH_2$—CHR—O)$_m$—$CH_2$—$CH_2$OCO—$CH_2$—$CH_2$COOH
$R_{10}$—($CH_2$—$CH_2$—O—)$_n$-co-($CH_2$—CHR—O)$_m$—$CH_2$—$CH_2$ $R_{10}$
$R_{10}$—($CH_2$—$CH_2$—O—)$_n$-b-($CH_2$—CHR—O)$_m$—$CH_2$—$CH_2$ $R_{10}$
$R_{10}$—$CH_2$O—($CH_2$—$CH_2$—O—)—CO—($CH_2$—CHR—O)$_m$—$CH_2$—$R_{10}$
$R_{10}$—$CH_2$O—($CH_2$—$CH_2$—O—)$_n$-b-($CH_2$—CHR—O)$_n$—$CH_2$—$R_{10}$
$R_{10}$—$CH_2$—$CH_2$—$CH_2$—O—($CH_2$—$CH_2$—O—)$_n$-co-($CH_2$—CHR—O)$_m$—$CH_2$—$CH_2$—$CH_2$—$R_{10}$
$R_{10}$—$CH_2$—$CH_2$—$CH_2$—O—($CH_2$—$CH_2$—O—)$_n$-b-($CH_2$—CHR—O)$_m$—$CH_2$—$CH_2$—$CH_2$—$R_{10}$
$R_{10}$—$CH_2$—$CH_2$—COO—($CH_2$—$CH_2$—O—)$_n$-co-($CH_2$—CHR—)$_m$—$CH_2$—$CH_2$—$CH_2$—$CH_2$—$R_{10}$
$R_{10}$—$CH_2$—$CH_2$—COO—($CH_2$—$CH_2$—O—)$_n$-b-($CH_2$—CHR—O)$_m$—$CH_2$—$CH_2$—O—CO—$CH_2$—$CH_2$—$R_{10}$
$R_{10}$—$CH_2$—$CH_2$—CONH—($CH_2$—$CH_2$—O—) 1-co-($CH_2$—CHR—O)$_m$—$CH_2$—$CH_2$—NH—CO—$CH_2$—$CH_2$—$R_{10}$
$R_{10}$—$CH_2$—$CH_2$—CONH—($CH_2$—$CH_2$—O—)$_n$-b-($CH_2$—CHR—O)$_m$—$CH_2$—$CH_2$—NH—CO—$CH_2$—$CH_2$—$R_{10}$ in which:
the R radical, being identical or different, represents —$CH_3$, —($CH_2$)$_x$—COOH; —($CH_2$)$_x$—$SO_3$H; ($CH_2$)$_x$—$PO_3H_2$; with x=1 to 8;
the $R_{10}$ radical, being identical or different, is —COOH, —$SO_3$H or —$PO_3H_2$;
n is an integer between 3 and 1000;
m is an integer between 0 and 200,
given that the n/m ratio is greater than 5, when m is non zero.

Preferably, R represents methyl, or else the radicals with x=2 to 3.

Preferably, n represents 4 to 30, especially 5 to 15.

It is obviously possible to use a mixture of various neutralizing agents.

Preferably, the neutralizing agent is chosen from the following structures:

$CH_3$—O—($CH_2$—$CH_2$—O—)$_n$-co-($CH_2$—CHR—O)$_m$—$CH_2$—$CH_2$ $R_{10}$
$CH_3$—O—($CH_2$—$CH_2$—O—)$_n$-co-($CH_2$—CHR—O)$_m$—$CH_2$—$CH_2CH_2$ $R_{10}$
$R_{10}$—($CH_2$—$CH_2$—O—)$_n$-co-($CH_2$—CHR—O)$_m$—$CH_2$—$CH_2$ $R_{10}$
$R_{10}$—$CH_2$O—($CH_2$—$CH_2$—O—)$_n$-co-($CH_2$—CHR—O)$_m$—$CH_2$—$R_{10}$ in which the $R_{10}$ radical is —COOH, —$SO_3$H or —$PO_3H_2$; preferably COOH; m is 0 to 200 and n is 3 to 1000, especially 4 to 30, or even 5 to 15.

Even more preferably, the neutralizing agent is chosen from the following structures:

$CH_3$—O—($CH_2$—$CH_2$—O—)—$CH_2$—$CH_2$ $R_{10}$
$CH_3$—O—($CH_2$—$CH_2$—O—)$_n$—$CH_2$—$CH_2CH_2$ $R_{10}$
$R_{10}$—($CH_2$—$CH_2$—O—)$_n$—$CH_2$—$CH_2$ $R_{10}$
$R_{10}$—$CH_2$O—($CH_2$—$CH_2$—O—)$_n$—$CH_2$—$R_{10}$ in which the $R_{10}$ radical is —COOH, —$SO_3$H or —$PO_3H_2$; preferably COOH; and n is 3 to 1000, especially 4 to 30, or even 5 to 15.

Mention may, in particular, be made of:
$CH_3$—O—($CH_2$—$CH_2$—O—)$_n$—$CH_2$—$CH_2$—$SO_3$H which may be named O-methyl, O'-(2-sulfoethyl)polyethylene glycol;
$CH_3$—O—($CH_2$—$CH_2$—O—)$_n$—$CH_2$—$CH_2$—$CH_2$COOH which may be named O-methyl, O'-(2-carboxypropyl)polyethylene glycol;
HOCO—$CH_2$—$CH_2$—O—)$_n$—$CH_2$—$CH_2$COOH which may be named O,O'-bis(2-carboxyethyl)polyethylene glycol; and
HOCO—$CH_2$O—($CH_2$—$CH_2$—O—)$_n$—$CH_2$—COOH which may be named O,O'-bis(2-carboxymethyl)polyethylene glycol;

with n=3 to 1000, especially 4 to 30, or even 5 to 15.

The neutralizing agents of type (vii) may especially be prepared by reaction of a polymer having hydroxyl or amine functional groups in the presence of an anhydride such as succinic or glutaric anhydride. Thus, for example, the reaction of a methoxyPEG-OH (or O-methyl-PEG) in the presence of glutaric anhydride makes it possible to prepare the corresponding PEG glutarate.

The polymers according to the invention can preferably be conveyed in an aqueous medium, that is to say that they are preferably water-soluble or water-dispersible. Dissolving or dispersing in water may be carried out by directly dissolving the polymer if it is soluble, or else by neutralizing the amine units so as to make the polymer soluble or dispersible in water.

Dissolving or dispersing in aqueous medium may also be carried out via an intermediate step of dissolving in an organic solvent followed by the addition of water before evaporation of the organic solvent.

Preferably, dissolving or dispersing in water may be carried out by mixing the polymer in pulverulent form with the neutralizing agent, then addition of water.

The neutralized polymers according to the invention find a most particular application in the field of cosmetics. They may be present in the composition in dissolved form, for example in water or an organic solvent especially ethanol, butyl acetate, isopropyl myristate or else in a silicone-based solvent such as volatile silicone oils, especially D5.

They may also be present in the form of an aqueous or organic or silicone-based dispersion, especially in one of these solvents.

They may be used in the cosmetic or pharmaceutical compositions in an amount of 0.01 to 50% by weight of dry matter, especially 0.1 to 30% by weight, or even 0.3 to 10% by weight, even better from 1 to 3% by weight, relative to the total weight of the composition.

The cosmetic or pharmaceutical compositions according to the invention comprise, besides said polymers, a physiologically acceptable, especially cosmetically or pharmaceutically acceptable, medium, that is to say a medium that is compatible with keratinous substances such as the skin of the face or body, the hair, eyelashes, eyebrows and nails.

The composition may thus comprise a hydrophilic medium comprising water or a mixture of water and hydrophilic organic solvent(s) such as alcohols and especially linear or branched $C_1$-$C_6$ monoalcohols, such as ethanol, tert-butanol, n-butanol, isopropanol or n-propanol, and polyols such as glycerol, digylcerol, propylene glycol, sorbitol, pentylene glycol, and polyethylene glycols; or else glycol ethers especially $C_2$ glycol ethers and hydrophilic $C_2$-$C_4$ aldehydes.

The water or mixture of water and hydrophilic organic solvents may be present in the composition according to the invention in an amount ranging from 0.1 to 99% by weight, relative to the total weight of the composition, and preferably from 10% to 80% by weight.

The composition may also comprise a fatty phase, comprised in particular of fatty substances that are liquid at ambient temperature (generally 25° C.) and/or fatty substances that are solid at ambient temperature such as waxes, pasty fatty substances, gums and mixtures thereof. These fatty substances may be of animal, vegetable, mineral or synthetic origin. This fatty phase may, moreover, contain lipophilic organic solvents.

As fatty substances that are liquid at ambient temperature, often called oils, that can be used in the invention, mention may be made of hydrocarbon-based oils of animal origin such as perhydrosqualene; hydrocarbon-based vegetable oils such as the liquid triglycerides of fatty acids having 4 to 10 carbon atoms such as heptanoic or octanoic acid triglycerides, or else sunflower, maize, soya bean, grape seed, sesame, apricot, macadamia, castor, or avocado oils, caprylic/capric acid triglycerides, jojoba oil or shea butter oil; linear or branched hydrocarbons of mineral or synthetic origin such as paraffin oils and derivatives thereof, Vaseline, polydecenes, hydrogenated polyisobutene such as parleam; synthetic esters and ethers especially of fatty acids such as for example Purcellin oil, isopropyl myristate, 2-ethylhexyl palmitate, 2-octyldodecyl stearate, 2-octyldodecyl eructate, isostearyl isostearate; hydroxylated esters such as isostearyl lactate, octyl hydroxystearate, octyldodecyl hydroxystearate, diisostearyl malate, triisocetyl citrate, and heptanoates, octanoates and decanoates of fatty alcohols; polyol esters such as propylene glycol dioctanoate, neopentyl glycol diheptanoate, diethylene glycol diisononanoate; and pentaerythritol esters; fatty alcohols having 12 to 26 carbon atoms such as octyldodecanol, 2-butyloctanol, 2-hexyldecanol, 2-undecylpentadecanol, oleyl alcohol; partially hydrocarbon-based and/or silicone-based fluoro oils; silicone oils such as volatile or non-volatile, linear or cyclic polymethylsiloxanes (PDMS) that are liquid or pasty at ambient temperature such as cyclomethicones or dimethicones, optionally comprising a phenyl group, such as phenyltrimethicones, phenyltrimethylsiloxy-diphenylsiloxanes, diphenylmethyldimethyltrisiloxanes, diphenyldimethicones, phenyldimethicones, polymethyl-phenylsiloxanes; and mixtures thereof.

These oils may be present in an amount ranging from 0.01 to 90%, and better from 0.1 to 85% by weight, relative to the total weight of the composition.

The composition according to the invention may also comprise one or more physiologically acceptable organic solvents.

These solvents may generally be present in an amount ranging from 0.1 to 90%, preferably from 0.5 to 85%, more preferably from 10 to 80% by weight, relative to the total weight of the composition, and better from 30 to 50%.

Mention may especially be made, besides the hydrophilic organic solvents mentioned above, of ketones that are liquid at ambient temperature such as methyl ethyl ketone, methyl isobutyl ketone, diisobutyl ketone, isophorone, cyclohexanone, acetone; propylene glycol ethers that are liquid at room temperature such as propylene glycol monomethyl ether, propylene glycol monomethyl ether acetate, dipropylene glycol mono-n-butyl ether; short-chain esters (having from 3 to 8 carbon atoms in total) such as ethyl acetate, methyl acetate, propyl acetate, n-butyl acetate, isopentyl acetate; ethers that are liquid at 25° C. such as diethyl ether, dimethyl ether or dichlorodiethyl ether; alkanes that are liquid at 25° C. such as decane, heptane, dodecane, isododecane, cyclohexane; cyclic aromatic compounds that are liquid at 25° C. such as toluene and xylene; aldehydes that are liquid at 25° C. such as benzaldehyde, acetaldehyde and mixtures thereof.

The term "wax", in the sense of the present invention, is understood to mean a lipophilic compound, which is solid at ambient temperature (25° C.), has a reversible solid/liquid phase change, that has a melting point greater than or equal to 25° C. which may range up to 120° C. On bringing the wax to the liquid state (melting), it is possible to make it miscible with the oils optionally present and to form a microscopically homogeneous mixture, but, on bringing the temperature of the mixture to ambient temperature, recrystallization of the wax in the oils of the mixture is obtained. The melting point of the wax may be measured using a differential scanning calorimeter (DSC), for example the calorimeter sold under the name DSC 30 by Mettler.

The waxes may be hydrocarbon-based, fluoro and/or silicone waxes and may be of vegetable, mineral, animal and/or synthetic origin. In particular, the waxes have a melting point above 30° C., and better above 45° C. As wax that can be used in the composition of the invention, mention may be made of beeswax, carnauba wax or candelilla wax, paraffin wax, microcrystalline waxes, ceresine or ozokerite; synthetic waxes such as polyethylene or Fischer-Tropsch waxes, silicone waxes such as alkyl or alkoxy dimethicones having from 16 to 45 carbon atoms.

The gums are generally high molecular weight polydimethylsiloxanes (PDMSs) or cellulose gums or polysaccharides and the pasty substances are generally hydrocarbon-based compounds such as lanolins and derivatives thereof or else PDMSs.

The nature and amount of the solid substances are a functional group of the desired mechanical properties and textures. By way of indication, the composition may contain from 0.1 to 50% by weight of waxes, relative to the total weight of the composition and better from 1 to 30% by weight.

The composition according to the invention may, in addition, comprise, in one particular phase, pigments and/or nacres and/or fillers commonly used in cosmetic compositions.

The composition may also comprise other coloring materials chosen from water-soluble dyes or liposoluble dyes well known to a person skilled in the art.

The term "pigments" should be understood to mean white or colored, mineral or organic particles of any shape which are insoluble in the physiological medium and which are intended to color the composition.

The term "fillers" should be understood to mean colorless or white, mineral or synthetic, lamellar or non-lamellar particles which are intended to give body or firmness to the composition, and/or softness, mattness and uniformity to the makeup.

The term "nacres" should be understood to mean iridescent particles of any shape, especially produced by certain mollusks in their shell or else synthesized. The pigments may be present in the composition in an amount of 0.01 to 25% by weight of the final composition, and preferably in an amount of 3 to 10% by weight. They may be white or colored, mineral or organic. Mention may be made of titanium, zirconium or cerium oxides, and also zinc, iron or chromium oxides, ferric blue, chromium hydrate, carbon black, ultramarines (aluminosilicate polysulfides), manganese pyrophosphate and certain metallic powders such as those of silver or aluminum. Mention may also be made of D&C pigments and lakes commonly used to confer a makeup effect on the lips and skin, which are calcium, barium, aluminum, strontium or zirconium salts.

The nacres may be present in the composition in an amount of 0.01 to 20% by weight, preferably at a content of around 3 to 10% by weight. Among the nacres that can be envisaged, mention may be made of natural mother-of-pearl, mica covered with titanium oxide, with iron oxide, with natural pigment or with bismuth oxychloride, and also colored titanium oxide-coated mica.

Among the lipsoluble or water-soluble dyes which may be present in the composition, alone or as a mixture, in an amount of 0.001 to 15% by weight, preferably 0.01 to 5% by weight and especially 0.1 to 2% by weight, relative to the total weight of the composition, mention may be made of the disodium salt of ponceau, the disodium salt of alizarine green, quinoline yellow, the trisodium salt of amaranth, the disodium salt of tartrazine, the monosodium salt of rhodamine, the disodium salt of fuchsin, xanthophyll, methylene blue, cochineal carmine, haloacid, azo or anthraquinone dyes, copper or iron sulfate, Soudan brown, Soudan red and ammatto, and also beet juice and carotene.

The composition according to the invention may comprise, in addition, one or more fillers, especially in an amount ranging from 0.01% to 50% by weight, relative to the total weight of the composition, preferably ranging from 0.02% to 30% by weight. The fillers may be mineral or organic and of any shape, platelet, spherical or oblong. Mention may be made of talc, mica, silica, kaolin, polyamide (Nylon®) powders, poly(β-alanine) powders and polyethylene powders, tetrafluoroethylene polymer (Teflon®) powders, lauroyl lysine, starch, boron nitride, hollow polymeric microspheres such as those made of polyvinylidene chloride/acrylonitrile such as Expancel® (Nobel Industrie), or made of acrylic acid copolymers (Polytrap® from Dow Corning) and silicone resin microbeads (Tospearls® from Toshiba, for example), particles of polyorganosiloxane elastomers, precipitated calcium carbonate, magnesium carbonate and hydrogen carbonate, hydroxyapatite, hollow silica microspheres (Silica Beads® from Maprecos), glass or ceramic microcapsules, or metal soaps derived from organic carboxylic acids having from 8 to 22 carbon atoms, preferably from 12 to 18 carbon atoms, for example zinc, magnesium or lithium stearate, zinc laurate or magnesium myristate.

The composition may moreover comprise an additional polymer such as a film-forming polymer. According to the present invention, "film-forming polymer" is understood to mean a polymer capable of forming, by itself alone or in the presence of an additional film-forming agent, a film that is continuous and adherent on a support, especially on keratinous substances. Among the film-forming polymers capable of being used in the composition of the present invention, mention may be made of synthetic polymers, of radical type or of polycondensate type, polymers of natural origin and mixtures thereof, in particular acrylic polymers, polyurethanes, polyesters, polyamides, polyureas or cellulose polymers such as nitrocellulose.

The composition may also advantageously comprise at least one surfactant which is generally present in an amount between 0.01% and 50% by weight, preferably between 0.1% and 40%, and even more preferably between 0.5% and 30%, relative to the total weight of the composition.

This surfactant may be chosen from anionic, amphoteric, non-ionic or cationic surfactants or mixtures thereof. The surfactants which are suitable for use in the present invention are especially, alone or as a mixture:

anionic surfactants among which mention may be made, alone or as mixtures, of the salts (in particular alkali metal, especially sodium salts, ammonium salts, amine salts, amino alcohol salts or magnesium salts) of the following compounds: alkyl sulfates, alkyl ether sulfates, alkylamido ether sulfates, alkylaryl polyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates, the alkyl or acyl radical of all these various compounds preferably comprising from 8 to 24 carbon atoms, and the aryl radical preferably denoting a phenyl or benzyl group.

Mention may also be made of the salts of fatty acids such as the salts of oleic, ricinoleic, palmitic and stearic acids, the acids of coconut oil or of hydrogenated coconut oil; acyl lactylates of which the acyl radical comprises 8 to 20 carbon atoms; alkyl-D-galactosideuronic acids and salts thereof and also polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and salts thereof, in particular those comprising from 2 to 50 ethylene oxide groups, and mixtures thereof.

non-ionic surfactants, among which mention may be made, alone or as mixtures, of polyethoxylated, polypropoxylated or polyglycerolated fatty acids, alcohols, α-diols or alkylphenols having a fatty chain comprising, for example, 8 to 18 carbon atoms, the number of ethylene oxide or propylene oxide groups possibly ranging, in particular, from 2 to 50 and the number of glycerol groups possibly ranging, in particular, from 2 to 30.

Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides comprising, on average, 1 to 5 glycerol groups and in particular 1.5 to 4; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, or amine oxides such as ($C_{10}$-$C_{14}$)alkylamine oxides or N-acylaminopropyl-morpholine oxides.

amphoteric surfactants, among which mention may be made, alone or as mixtures, of aliphatic secondary or tertiary amine derivatives, in which the aliphatic radical is a linear or branched chain comprising 8 to 22 carbon atoms and having at least one water-solubilizing anionic group (for example carboxylate, sulfonate, sulfate, phosphate or phosphonate); mention may also be made of ($C_8$-$C_{20}$)alkyl betaines, sulfobetaines, ($C_8$-$C_{20}$)alkylamido, ($C_1$-$C_6$)alkyl betaines such as cocoamidopropyl betaine or ($C_8$-$C_{20}$)alkylamido ($C_1$-$C_6$)alkyl sulfobetaines;

cationic surfactants, among which mention may be made, alone or as mixtures, of

A) quaternary ammonium salts of the following general formula (XVI):

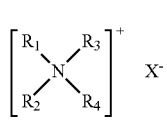

(XVI)

in which X is an anion chosen from halides (chloride, bromide or iodide) or ($C_2$-$C_6$)alkyl sulfates, more particularly methyl sulfate, phosphates, alkyl or alkylaryl sulfonates, and anions derived from an organic acid such as the acetate or lactate; and a) the $R_1$ to $R_3$ radicals, which may be identical or different, represent a linear or branched aliphatic radical comprising 1 to 4 carbon atoms, or an aromatic radical such as an aryl or alkylaryl radical. The aliphatic radicals may comprise heteroatoms such as, in particular, oxygen, nitrogen, sulfur or halogens. The aliphatic radicals are, for example, chosen from alkyl, alkoxy or alkylamide radicals;

$R_4$ denotes a linear or branched alkyl radical, comprising from 16 to 30 carbon atoms.

Preferably, the cationic surfactant is a behenyltrimethylammonium salt (for example chloride).

b) the $R_1$ and $R_2$ radicals, which may be identical or different, represent a linear or branched aliphatic radical comprising from 1 to 4 carbon atoms, or an aromatic radical such as an aryl or alkylaryl radical. The aliphatic radicals may comprise heteroatoms such as, in particular, oxygen, nitrogen, sulfur or halogens. The aliphatic radicals are, for example, chosen from the alkyl, alkoxy, alkylamide and hydroxyalkyl, comprising around 1 to 4 carbon atoms;

$R_3$ and $R_4$, being identical or different, denote a linear or branched alkyl radical comprising from 12 to 30 carbon atoms, said radical comprising at least one ester or amide functional group;

$R_3$ and $R_4$ are essentially chosen from ($C_{12}$-$C_{22}$)alkylamido ($C_2$-$C_6$)alkyl or ($C_{12}$-$C_{22}$)alkyl acetate radicals.

Preferably, the cationic surfactant is a stearamidopropyldimethyl(myristylacetate)ammonium salt (for example chloride).

B) imidazolinium quaternary ammonium salts, such as that of formula (XVII) below:

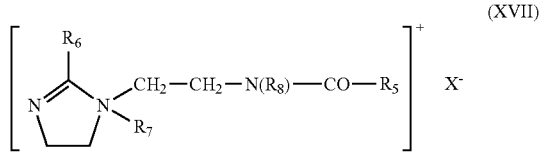

(XVII)

in which $R_5$ represents an alkenyl or alkyl radical comprising from 8 to 30 carbon atoms, for example derivatives of tallow fatty acids, $R_6$ represents a hydrogen atom, a $C_1$-$C_4$ alkyl radical or an alkenyl or alkyl radical comprising from 8 to 30 carbon atoms, $R_7$ represents a $C_1$-$C_4$ alkyl radical, $R_8$ represents a hydrogen atom or a $C_1$-$C_4$ alkyl radical, X is an anion chosen from the group of halides, phosphates, acetates, lactates, alkyl sulfates and alkyl or alkylaryl sulfonates. Preferably, $R_5$ and $R_6$ denote a mixture of alkenyl or alkyl radicals comprising from 12 to 21 carbon atoms, for example derived from tallow fatty acids, $R_7$ denotes methyl and $R_8$ denotes hydrogen. Such a product is, for example, Quaternium-27(CTFA 1997) or Quaternium-83 (CTFA 1997) sold under the names REWOQUAT W 75, W90, W75PG, W75HPG by WITCO;

C) quaternary diammonium salts of formula (XVIII):

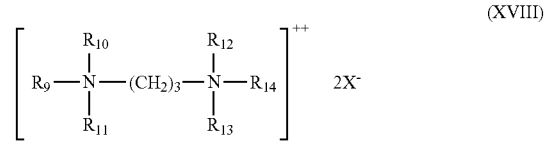

(XVIII)

in which $R_9$ denotes an aliphatic radical comprising around 16 to 30 carbon atoms, $R_{10}$, $R_{11}$, $R_{12}$, $R_{13}$ and $R_{14}$, being identical or different, are chosen from hydrogen or an alkyl radical comprising from 1 to 4 carbon atoms, and X is an anion chosen from the group of halides, acetates, phosphates, nitrates and methyl sulfates. Such quaternary diammonium salts especially comprise propane tallow diammonium dichloride;

D) quaternary ammonium salts comprising at least one ester functional group of formula (XIX) below:

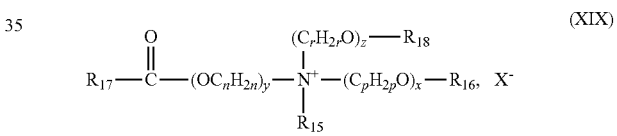

(XIX)

in which:

$R_{15}$ is chosen from $C_1$-$C_6$ alkyl radicals and $C_1$-$C_6$ dihydroxyalkyl or hydroxyalkyl radicals;

$R_{16}$ is chosen from:
the

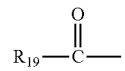

radical;

linear or branched, saturated or unsaturated $C_1$-$C_{22}$ hydrocarbon-based $R_{20}$ radicals;

hydrogen atoms;

$R_{18}$ is chosen from:
the

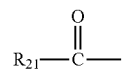

radical;

linear or branched, saturated or unsaturated $C_1$-$C_6$ hydrocarbon-based $R_{22}$ radicals;

hydrogen atoms;

$R_{17}$, $R_{19}$ and $R_{21}$, being identical or different, are chosen from linear or branched, saturated or unsaturated $C_7$-$C_{22}$ hydrocarbon-based radicals;

n, p and r, being identical or different, are integers ranging from 2 to 6;

y is an integer ranging from 1 to 10;

x and z, being identical or different, are integers ranging from 0 to 10; and $X^-$ is an organic or inorganic, simple or complex anion, on condition that the sum x+y+z is equal to 1 to 15, that when x is equal to 0 then $R_{16}$ denotes $R_{20}$ and that when z equals 0 then $R_{18}$ denotes $R_{22}$.

The composition according to the invention may also comprise ingredients commonly used in cosmetics, such as vitamins, fragrances, pearlescent agents, thickeners, gelling agents, trace elements, demulcent agents, sequestering agents, fragrances, basifying or acidifying agents, preservatives, sunscreens, surfactants, antioxidants, agents for combating hair loss, antidandruff agents, propellants or ceramides, or mixtures thereof. Of course, a person skilled in the art will be sure to choose this or these optional additional compounds, and/or their amount, so that the advantageous properties of the composition according to the invention are not, or are not substantially, impaired by the envisaged addition.

The composition according to the invention may be in the form of a suspension, a dispersion, in particular an oil-in-water dispersion, by virtue of vesicles; an oily solution optionally thickened or even gelled; an oil-in-water, water-in-oil or multiple emulsion; a gel or a foam; an oily or emulsified gel; a dispersion of vesicles, especially lipid vesicles; a two-phase or multiphase lotion or a spray. This composition may have the appearance of a lotion, a cream, an ointment, a soft paste, a salve, a cast or molded, especially in stick or dish form, solid or else a compacted solid.

A person skilled in the art will be able to choose the appropriate pharmaceutical form, and also its preparation method, based on his general knowledge, by taking into account, on the one hand, the nature of the constituents used, especially their solubility in the support, and on the other hand, the application envisaged for the composition.

The cosmetic composition according to the invention may be in the form of a care and/or makeup product for the skin of the body or face, the lips and the hair, of a suntan or self-tanning product, or even of a hair product.

In particular, it finds a particularly advantageous application in the hair field, especially for form retention of the hairstyle or hair shaping. The hair compositions are preferably shampoos, gels, hair setting lotions, blow-drying lotions, fixing and styling compositions such as lacquers or sprays. The lotions may be packaged in various forms, especially in spray, pump dispensers or in aerosol containers in order to provide application of the composition in sprayed form or in foam form.

In one preferred embodiment, the compositions according to the invention may be used for washing or treating keratinous substances such as the hair, skin, eyelashes, eyebrows, nails, lips, scalp and more particularly the hair.

The compositions according to the invention may be detergent compositions such as shampoos, shower gels and foam baths. In this embodiment of the invention, the compositions comprise at least one washing, generally aqueous, base which may comprise from 5 to 35% of surfactant.

They may also be in the form of rinse-out or leave-in conditioner, perming, hair straightening, dyeing or bleaching compositions, or else in the form of rinse-out compositions, to be applied before or after a dyeing, bleaching, perming or hair straightening operation or else between the two steps of a perming or a hair straightening operation.

When the composition is present in the form of a conditioner optionally to be rinsed out, it advantageously contains at least one cationic surfactant, for example at a concentration generally between 0.1 and 10% by weight and preferably from 0.5 to 5% by weight relative to the total weight of the composition.

The compositions of the invention may also be in the form of washing compositions for the skin, and in particular in the form of solutions or gels for the bath or shower or makeup-removing products.

The compositions according to the invention may also be in the form of aqueous or aqueous/alcoholic lotions for caring for the skin and/or hair.

Another subject of the invention is a method for cosmetic treatment of keratinous substances such as the skin or hair, especially a method for the form retention of the hairstyle, cosmetic treatment, care, washing, makeup removal and/or making up, keratinous substances, especially the skin of the body or face, nails, hair, eyelashes, eyebrows, characterized in that it consists in applying, to said keratinous substances, a cosmetic composition as defined previously, then in optionally rinsing with water.

The invention is illustrated in greater detail in the following examples.

In these examples, the neutralizing agent is a poly(ethylene glycol) bis(carboxymethyl)ether with MW=600 g/mol, sold by Aldrich: HOCO—$CH_2$O—($CH_2$—$CH_2$—O—)$_n$—$CH_2$—COOH.

EXAMPLE 1

Introduced into a 500 ml beaker equipped with a magnetic bar were 10 g of poly(4-vinylpyridine) with MW=160,000 g/mol (Aldrich) and the indicated amount of neutralizing agent was added. This mixture, in the form of a white paste, was heated at 60° C. for 30 minutes, then 90 ml of water were added. The mixture was kept at 60° C. for 1 hour. A partially or completely neutralized polymer solution was obtained.

In an identical manner, various homopolymers and copolymers were prepared that were neutralized with the same neutralizing agent.

The results are given in the table below.

| Polymer | MW | Neutralizing agent* | Solution** |
|---|---|---|---|
| Poly(4-vinylpyridine) | 60,000 | 0.5 | pH = 3.72<br>22.9% DM |
| Polyvinylpyridine | 60,000 | 0.25 | pH = 5.11<br>18.5% DM |
| Poly(4-vinylpyridine) | 160,000 | 0.125 | pH = 4.69<br>15.01% DM |
| Poly(4-vinylpyridine) | 160,000 | 0.5 | pH = 3.53<br>23.4% DM |
| Poly(vinylpyridine) | 5000 | 0.5 | pH = 3.42<br>8.42% DM |
| Poly(styrene-co-vinyl pyridine) 30/70 | 130,000 | 0.5 | pH = 3.72<br>8.45% DM |
| Poly(styrene-co-vinyl pyridine) 30/70 | 130,000 | 0.25 | pH = 3.80<br>9.02% DM |
| Poly(styrene-co-vinyl pyridine) 30/70 | 220,000 | 0.25 | pH = 3.08<br>9.09% DM |

| Polymer | MW | Neutralizing agent* | Solution** |
|---|---|---|---|
| Poly(styrene-co-vinyl pyridine) 30/70 | 220,000 | 0.5 | pH = 3.42 8.45% DM |

DM: dry matter
*neutralizing agent: amount, in molar equivalent, of neutralizing agent added
**pH and amount of dry matter in the solution obtained For comparison, the following were prepared:

| Polymer | MW | Neutralizing agent* | Solution** |
|---|---|---|---|
| Polyvinylpyridine | 160,000 | Neutralized with 1 eq. HCl | pH = 1.1 10.9% DM |
| Polyvinylpyridine | 60,000 | Neutralized with 1 eq. HCl | pH = 1 9.75% DM |
| Polyvinylpyridine | 5000 | Neutralized with 1 eq. HCl | pH = 1 8.68% DM |
| Poly(styrene-co-vinylpyridine) 30/70 | 220,000 | Neutralized with 1 eq. HCl | pH = 1 7.5% DM |

EXAMPLE 2

In an identical manner to Example 1, the following were neutralized with a $CO_2H$-PEG-$CO_2H$ neutralizing agent:
copolymers based on dimethylaminopropyl methacrylamide (DMAPMA) and on vinylpyrrolidone (VP): commercial product Styleze CC10 from ISP;
a DMAPMA homopolymer;
poly(vinylamine/vinylformamide) copolymers VA/VF: commercial products from BASF: Lupamin 1595 (degree of hydrolysis of VA≥90%); Lupamin 9095 (degree of hydrolysis of VA≥90%), Lupamin 4595 (degree of hydrolysis of VA≥90%); Lupamin 9030 (degree of hydrolysis of VA≥30%); and
poly(allylamine) homopolymers.

| Polymer | MW | Neutralizing agent* | Solution** |
|---|---|---|---|
| Poly(DMAPMA/VP) | | 0.5 | pH = 2.78 6.85% DM |
| Poly(DMAPMA/VP) | | 3 | pH = 11.38 24.9% DM |
| Poly(DMAPMA) | | 0.5 | pH = 5.79 29.9% DM |
| Poly(VA/VF), Lupamin 1595 | <10,000 | 0.25 | pH = 3.22 55.20% DM |
| Poly(VA/VF), Lupamin 9095 | 340,000 | 0.25 | pH = 3.20 25.97% DM |
| Poly(VA/VF), Lupamin 4595 | 45,000 | 0.5 | pH =3.05 53.6% DM |
| Poly(VA/VF), Lupamin 3095 | 340,000 | 1 | pH = 2.85 36.60% DM |
| Poly(VA/VF), Lupamin 3095 | 340,000 | 0.5 | pH = 2.99 30.2% DM |
| Poly(VA/VF), Lupamin 3095 | 340,000 | 0.125 | pH = 3.64 16.8% DM |
| Poly(VA/VF), Lupamin 3095 | 340,000 | 0.5 | pH = 4.36 19.6% DM |
| Poly(allylamine) | 17,000 | 0.06 | pH = 10.06 20.5% DM |
| Poly(allylamine) | 17,000 | 0.2 | pH = 8.75 30.9% DM |
| Poly(allylamine) | 17,000 | 1 | pH = 3.16 34.1% DM |
| Poly(allylamine) | 65,000 | 0.06 | pH = 10.29 17.7% DM |
| Poly(allylamine) | 65,000 | 0.2 | pH = 8.70 18.9% DM |
| Poly(allylamine) | 65,000 | 1 | pH = 3.45 30.2% DM |
| Poly(allylamine) | 3000 | 0.2 | pH = 9.84 44.1% DM |
| Poly(allylamine) | 3000 | 1 | pH = 3.43 13.6% DM |

For comparison, the following were prepared:

| Polymer | MW | Neutralizing agent* | Solution** |
|---|---|---|---|
| Polyallylamine | 17,000 | Neutralized with 1 eq. HCl | 7.09% DM |
| Polyallyamine | 65,000 | Neutralized with 1 eq. HCl | 6.8% DM |
| Polyallyamine | 3000 | Neutralized with 1 eq. HCl | 40.0% DM |

EXAMPLE 3

In an identical manner to Example 1, poly(diallylamine) homopolymers were neutralized with the same neutralizing agent.

Poly(diallylamine) were synthesized as follows: diallylamine (5.0 g, 0.0515 mol) was dissolved in 6.18 g (10% excess) of concentrated hydrochloric acid (36% solution). The temperature was kept at 0° C., and the solution was then purged with argon.

The initiator (V50: 2,2'-azo-bis(2-amidinopropane) dihydrochloride) (0.14 g, 1 mol %) was added and the mixture was again purged with argon then placed in an oil bath at 60° C. for 24 hours. The viscose yellow solution obtained was diluted (1 volume) with water of HPLC quality. The solution was then cooled by a bath of ice and ethanol. 2 eq. of sodium hydroxide were added very slowly, then the precipitated polymer was filtered, washed with HPLC quality water and freeze dried. This polymer could then be neutralized.

By way of comparison, a neutralization was carried out with 1N HCl (10% aqueous solution) in a stoichiometric amount.

| | Neutralizing agent | Form |
|---|---|---|
| Example A | 1 eq. of neutralizing agent according to the invention | 26% DM aqueous solution |
| Example B | 0.75 eq. of neutralizing agent according to the invention | 19% DM aqueous solution |

-continued

|  | Neutralizing agent | Form |
|---|---|---|
| Example C | 0.5 eq. of neutralizing agent according to the invention | 19% DM aqueous solution |
| Example D | 0.25 eq. of neutralizing agent according to the invention | 14% DM aqueous solution |
| Counterexample E | 1 eq. HCl | |

*DM: dry matter

1% of active material (AM) of the above A and E neutralized polymers was introduced into a surfactant base comprising 12.5% AM of lauryl ether sulfate and 2.5% AM of cocoyl betaine, in water.

With the composition according to the invention, a good disentangling in a wet medium and a good cosmetic quality (feel, softness) in a dry medium were observed. Much better disentangling and smoothing were observed with the composition according to the invention relative to the composition comprising the counterexample E.

EXAMPLE 4: STYLING LOTION

Introduced into a pump dispenser were:
6% AM of an aqueous solution of polymer A from Example 3;
qs preservative; and
qs for 100% water.

The polymer solution was sprayed on to a 1.5 g lock of hair for 5 seconds. The lock was then wound around a 1 cm diameter curler, then dried at 70° C. for 30 minutes. Next, the lock was unwound.

The same thing was carried out replacing the polymer A with the polymer E (counterexample).

The following were noted for the hairstyle treated with the composition according to the invention in comparison with the hairstyle treated with the counterexample: a better hold on the locks of the hair style and the curls when they are present, an improved feel, especially in terms of softness, and also better disentangling.

The invention claimed is:

1. A cosmetic composition comprising, in a cosmetically acceptable medium:
at least one cationic ethylenic polymer comprising at least one amine functional group chosen from primary amine functional groups that can be protonated, secondary amine functional groups that can be protonated and tertiary amine functional groups that can be protonated and comprising at least one neutralizing agent, wherein said at least one amine functional group being at least partially neutralized by the at least one neutralizing agent, wherein the at least one neutralizing agent is chosen from polymers having the following structures:

$CH_3-O-(CH_2-CH_2-O-)_n\text{-co-}(CH_2-CHR-O)_m-CH_2-R_{10}$
$CH_3-O-(CH_2-CH_2-O-)_n\text{-b-}(CH_2-CHR-O)_m-CH_2-R_{10}$
$CH_3-O-(CH_2-CH_2-O-)_n\text{-co-}(CH_2-CHR-O)_m-CH_2-CH_2 R_{10}$
$CH_3-O-(CH_2-CH_2-O-)_n\text{-b-}(CH_2-CHR-O)_m-CH_2-CH_2 R_{10}$
$CH_3-O-(CH_2-CH_2-O-)_n\text{-co-}(CH_2-CHR-O)_m-CH_2-CH_2CH_2 R_{10}$
$CH_3-O-(CH_2-CH_2-O-)_n\text{-b-}(CH_2-CHR-O)_m-CH_2-CH_2CH_2 R_{10}$
$CH_3-O-(CH_2-CH_2-O-)_n\text{-co-}(CH_2-CHR-O)_m-CH_2-CH_2OCO-CH_2-CH_2COOH$
$CH_3-O-(CH_2-CH_2-O-)_n\text{-b-}(CH_2-CHR-O)_m-CH_2-CH_2OCO-CH_2-CH_2COOH$
$R_{10}-(CH_2-CH_2-O-)_n\text{-co-}(CH_2-CHR-O)_m-CH_2-CH_2 R_{10}$
$R_{10}-(CH_2-CH_2-O-)_n\text{-b-}(CH_2-CHR-O)_m-CH_2-CH_2 R_{10}$
$R_{10}-CH_2O-(CH_2-CH_2-O-)_n\text{-co-}(CH_2-CHR-O)_m-CH_2-R_{10}$
$R_{10}-CH_2O-(CH_2-CH_2-O-)_n\text{-b-}(CH_2-CHR-O)_m-CH_2-R_{10}$
$R_{10}-CH_2-CH_2-CH_2-O-(CH_2-CH_2-O-)_n\text{-co-}(CH_2-CHR-O)_m-CH_2-CH_2-CH_2-R_{10}$
$R_{10}-CH_2-CH_2-CH_2-O-(CH_2-CH_2-O-)_n\text{-b-}(CH_2-CHR-O)_m-CH_2-CH_2-CH_2-R_{10}$
$R_{10}-CH_2-CH_2-COO-(CH_2-CH_2-O-)_n\text{-co-}(CH_2-CHR-O)_m-CH_2-CH_2-O-CO-CH_2-CH_2-R_{10}$
$R_{10}-CH_2-CH_2-COO-(CH_2-CH_2-O-)_n\text{-b-}(CH_2-CHR-O)_m-CH_2-CH_2-O-CO-CH_2-CH_2-R_{10}$
$R_{10}-CH_2-CH_2-CONH-(CH_2-CH_2-O-)_n\text{-co-}(CH_2-CHR-O)_m-CH_2-CH_2-NH-CO-CH_2-CH_2-R_{10}$
$R_{10}-CH_2-CH_2-CONH-(CH_2-CH_2-O-)_n\text{-b-}(CH_2-CHR-O)_m-CH_2-CH_2-NH-CO-CH_2-CH_2-R_{10}$ wherein:
R is chosen from $-CH_3$, $-(CH_2)_x-COOH$; $-(CH_2)_x-SO_3H$; and $(CH_2)_x-PO_3H_2$; wherein x is chosen from an integer ranging from 1 to 8;
$R_{10}$ is chosen from $-COOH$, $-SO_3H$ and $-PO_3H_2$;
n is chosen from an integer ranging from 3 to 1000;
m is chosen from an integer ranging from 0 to 200, with the proviso that when m is not 0, the n/m ratio is greater than 5
and at least one cosmetic additive selected from the group consisting of water or a mixture of water and hydrophilic organic solvent, waxes, pasty fatty substances, gums, pigments, nacres, fillers, water-soluble dyes, liposoluble dyes, a film-forming polymer other than said at least one cationic ethylenic polymer, surfactant, vitamins, pearlescent agents, thickeners, gelling agents, sequestering agents, fragrances, basifying or acidifying agents, preservatives, sunscreens, antioxidants, agents for combating hair loss, antidandruff agents, propellants and ceramides.

2. The composition according to claim 1, wherein the at least one neutralizing agent is chosen from:
$CH_3-O-(CH_2-CH_2-O-)_n-CH_2-CH_2 R_{10}$;
$CH_3-O-(CH_2-CH_2-O-)_n-CH_2-CH_2CH_2 R_{10}$;
$R_{10}-(CH_2-CH_2-O-)_n-CH_2-CH_2 R_{10}$; and
$R_{10}-CH_2O-(CH_2-CH_2-O-)_n-CH_2-R_{10}$,
wherein $R_{10}$ is chosen from $-COOH$, $-SO_3H$ and $-PO_3H_2$; and n is an integer chosen from 3 to 1000.

3. The composition according to claim 1, wherein the at least one cationic ethylenic polymer is present in an amount ranging from 0.01 to 50% by weight of dry matter relative to the total weight of the cosmetic composition.

4. The composition according to claim 1, further comprises at least one constituent chosen from:

water,
hydrophilic organic solvents chosen from linear or branched $C_1$-$C_6$ monoalcohols, polyols and hydrophilic $C_2$-$C_4$ aldehydes;
waxes, pasty fatty substances, and gums;
lipophilic organic solvents;
hydrocarbon-based oils of animal origin;
hydrocarbon-based vegetable oils chosen from liquid triglycerides of fatty acids having 4 to 10 carbon atoms sunflower oils, maize oils, soya bean oils, grape seed oils, sesame oils, apricot oils, macadamia oils, castor oils, avocado oils, caprylic/capric acid triglycerides, jojoba oil and shea butter oil;
linear or branched hydrocarbons of mineral or synthetic origin chosen from paraffin oils, vaseline, polydecenes, and hydrogenated polyisobutene;
synthetic esters and ethers chosen from Purcellin oil, isopropyl myristate, 2-ethylhexyl palmitate, 2-octyldodecyl stearate, 2-octyldodecyl erucate, and isostearyl isostearate;
hydroxylated esters chosen from isostearyl lactate, octyl hydroxystearate, octyldodecyl hydroxystearate, diisostearyl malate, triisocetyl citrate, and heptanoates of fatty alcohols, octanoates of fatty alcohols and decanoates of fatty alcohols;
polyol esters chosen from propylene glycol dioctanoate, neopentyl glycol diheptanoate, diethylene glycol diisononanoate; and pentaerythritol esters;
fatty alcohols having 12 to 26 carbon atoms;
partially hydrocarbon-based or silicone-based fluoro oils;
silicone oils chosen from volatile or non-volatile, linear or cyclic polymethylsiloxanes (PDMS) that are liquid or pasty at ambient temperature optionally comprising a phenyl group;
ketones that are liquid at ambient temperature;
polypropylene glycol ethers that are liquid at ambient temperature;
short-chain esters (having from 3 to 8 carbon atoms in total);
ethers that are liquid at 25° C.; alkanes that are liquid at 25° C.; cyclic aromatic compounds that are liquid at 25° C.; aldehydes that are liquid at 25° C.; and
pigments, nacres, fillers; water-soluble dyes; liposoluble dyes; polymers; anionic surfactants, amphoteric surfactants, non-ionic surfactants, cationic surfactants; vitamins, fragrances, thickeners, gelling agents, trace elements, demulcent agents, sequestering agents, fragrances, basifying agents, acidifying agents, preservatives, sunscreens, antioxidants, agents for combating hair loss, antidandruff agents, propellants and ceramides.

5. The composition according to claim 1, wherein the neutralizing agent is poly(ethylene glycol) bis(carboxymethyl) ether.

6. The composition according to claim 5, wherein the at least one cationic ethylenic polymer is poly(vinylamine-vinylformamide).

7. The composition according to claim 1, wherein the at least one cationic ethylenic polymer comprises at least one residue of monomers of formula (I):

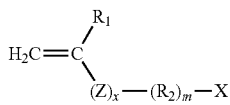

wherein:
$R_1$ is chosen from hydrogen and linear or branched, hydrocarbon-based radicals of $C_pH_{2p+1}$ type, wherein p is chosen from an integer between 1 and 12;
Z is a divalent group chosen from —COO—, —CONH—, —CONCH$_3$—, —OCO— or —O—, —SO$_2$—, —CO—O—CO— and —CO—CH$_2$—CO—;
x is 0 or 1, preferably 1;
$R_2$ is chosen from saturated or unsaturated, optionally aromatic, linear, branched or cyclic, carbon-based divalent radical having 1 to 30 carbon atoms, which may comprise 1 to 18 heteroatoms chosen from O, N, S, F, Cl, Br, Si and P;
m is 0 or 1;
X is chosen from:
  (a) guanidino groups;
  (b) amidino groups;
  (c) groups of formula —N($R_6$)($R_7$), wherein $R_6$ and $R_7$ are independently chosen from:
(i) a hydrogen atom;
(ii) a linear, branched or cyclic, saturated or unsaturated, optionally aromatic alkyl group comprising from 1 to 18 carbon atoms, optionally comprising 1 to 10 heteroatoms chosen from O, N, S, F, Si and P; and
(iii) $R_6$ and $R_7$ form, together with the nitrogen atom they are attached to, a ring of formula:

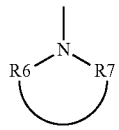

wherein the ring is saturated or unsaturated, optionally aromatic, and comprises from 5 to 8 atoms chosen from carbon, O, S and N; said first ring optionally being fused with at least one other ring chosen from, saturated or unsaturated, optionally aromatic rings comprising 5 to 7 atoms chosen from carbon, O, S and N;
(c) rings chosen from:

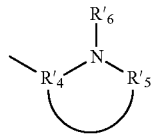

wherein $R'_4$ and $R'_5$ form, together with the nitrogen atom they are attached to, a saturated or unsaturated, optionally aromatic, ring comprising 5 to 8 atoms chosen from, carbon, O, S and N; said ring optionally being fused with at least one other ring chosen from, saturated or unsaturated, optionally aromatic, rings comprising 5 to 7 atoms chosen from carbon, O, S and N;
and $R'_6$ is chosen from H, —CH$_3$ and —C$_2$H$_5$;
wherein said at least one residue of monomers of formula (I) comprises at least one at least one amine functional group chosen from primary amine functional groups, secondary amine functional groups and tertiary amine functional groups, wherein said at least one amine functional group can be protonated at a pH ranging from 1 to 12.

8. The composition according to claim 7, wherein the monomers of formula (I) are chosen from dimethylaminopropyl (meth)acrylamide, dimethylaminoethyl (meth)acrylamide, diethylaminoethyl (meth)acrylate, dimethylaminoethyl (meth)acrylate, tert-butylaminoethyl (meth)acrylate, morpholinoethyl (meth)acrylate, vinylimidazole, vinylpyridine, vinylamine, allylamine, and the monomers below:

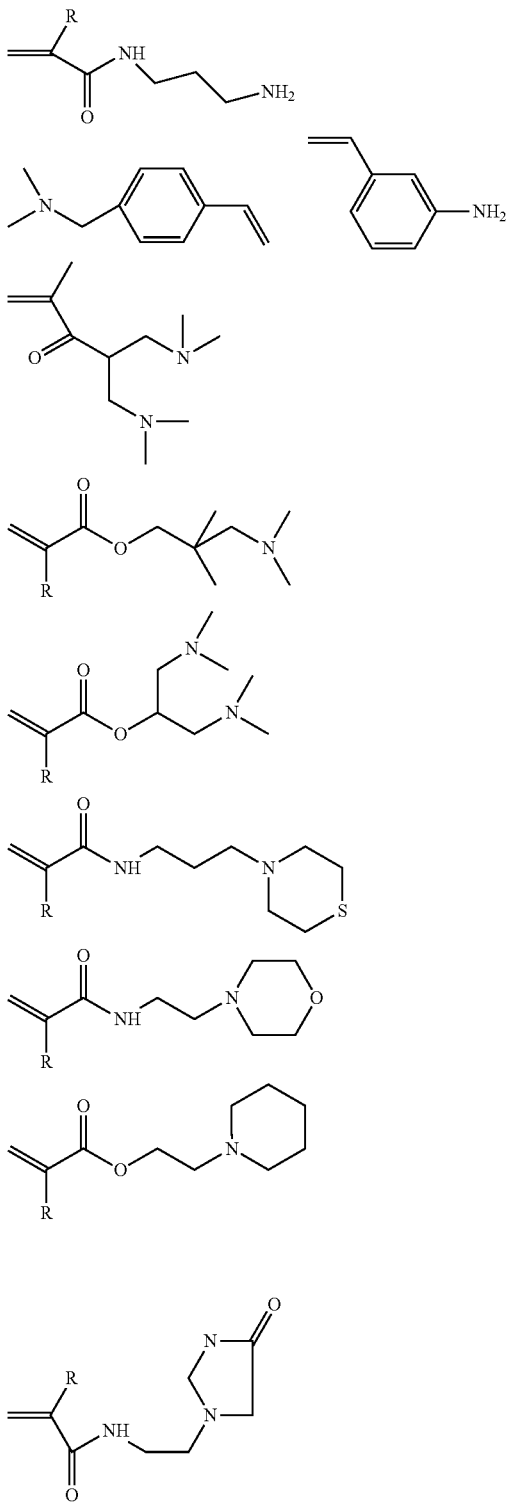

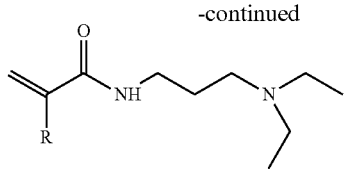

wherein R is chosen from hydrogen and methyl.

9. The composition according to claim 1, wherein the at least one cationic ethylenic polymer comprises at least one residue of monomers of formula (II):

wherein $R_3$ is chosen from hydrogen and linear, branched or cyclic, saturated or unsaturated, optionally aromatic, carbon-based radicas1 having 1 to 30 carbon atoms, optionally comprising 1 to 18 heteroatoms chosen from O, N, S, F, Cl, Br, Si and P, wherein the at least one monomer of formula (II) comprises at least one amine functional group chosen from primary, secondary and tertiary amine functional groups, wherein the at least one amine functional group can be protonated at a pH ranging from 1 to 12.

10. The composition according to claim 9, wherein the monomers of formula (II) are chosen from N-methyldiallylamine and diallylamine.

11. The composition according to claim 1, wherein the polymer comprises at least one residue of monomers of formula (III):

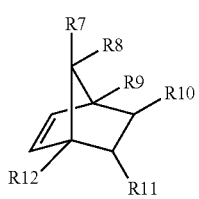

wherein $R_7$, $R_8$, $R_9$, $R_{10}$, $R_{11}$, and $R_{12}$, independently of one another, are chosen from:
a hydrogen atom;
an —$NR_{13}R'_{13}$ groups, wherein $R_{13}$ and $R'_{13}$, independently of one another, are chosen from hydrogen and linear, branched or cyclic, saturated or unsaturated, optionally aromatic alkyls comprising from 1 to 18 carbon atoms, optionally comprising 1 to 10 heteroatoms chosen from O, N, S, F, Si and P; and
a linear, branched or cyclic, saturated or unsaturated, optionally aromatic, carbon-based radicals having 1 to 30 carbon atoms, optionally comprising 1 to 18 heteroatoms chosen from O, N, S, F, Si and P,
wherein monomers of formula (III) comprise at least one amine functional group chosen from primary amine functional group, secondary amine functional group and tertiary amine functional groups, wherein the amine functional group can be protonated at a pH ranging from 1 to 12.

12. The composition according to claim 11, wherein the monomers of formula (III) are chosen from:

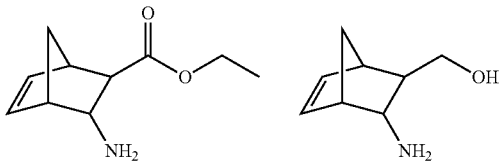

13. The composition according to claim 1, wherein the at least one cationic ethylenic polymer further comprises at least one residue of at least one additional monomer in an amount ranging from 0.01 to 99% by weight relative to the weight of the at least one cationic ethylenic polymer.

14. The composition according to claim 13, wherein the at least additional monomer is chosen from:

(i) (meth)acrylic acid esters of formula $CH_2=CHCOOR'_1$ or $CH_2=C(CH_3)COOR'_1$ wherein $R'_1$ is chosen from linear, branched or cyclic, saturated or unsaturated, optionally aromatic carbon-based radicals having 1 to 30 carbon atoms, optionally comprising 0 to 2 ether functional groups (—O—) and optionally 0 to 12 functional groups chosen from —OH (hydroxyl), —OR' with R' being chosen from $C_1$-$C_6$ alkyl (alkoxy), —CN, —X (halogen), —CO—, —SO$_3$H, —COOH, —OCOO—, —COO—, —OCONR—, —OCONH—, —NH—CONH—, —NR—CONR—, —CF$_3$, —CN, epoxy, —NHCO—, —N(R)CO— wherein R is chosen from linear or branched $C_1$-$C_{22}$ alkyls optionally comprising 1-12 heteroatoms;

(ii) (meth)acrylic acid amides of formula $CH_2=CHCONR'_2R''_2$ or $CH_2=C(CH_3)CONR'_2R''_2$, wherein $R'_2$, $R''_2$, are independently chosen from hydrogen and linear, branched or cyclic, saturated or unsaturated, optionally aromatic, carbon-based radicals having 1 to 30 carbon atoms, optionally comprising 0 to 2 ether functional groups (—O—) and optionally 0 to 12 functional groups chosen from —OH (hydroxyl), —OR' with R' being chosen from $C_1$-$C_6$ alkyls (alkoxy), —CN, —X (halogen), —CO—, —SO$_3$H, —COOH, —OCOO—, —COO—, —OCONR—, —OCONH—, —NH—CONH—, —NR—CONR—, —CF$_3$, —CN, epoxy, —NHCO—, —N(R)CO—, wherein R is chosen from linear or branched $C_1$-$C_{22}$ alkyls optionally comprising 1-12 heteroatoms;

(iii) vinyl esters of formula $CH_2=CH$—OCO—$R'_3$ or $CH_2=C(CH_3)$—OCO—$R'_3$, wherein $R'_3$ is chosen from linear, branched or cyclic, saturated or unsaturated, optionally aromatic, carbon-based radicals having 1 to 30 carbon atoms, optionally comprising 0 to 2 ether functional groups (—O—) and optionally 0 to 12 functional groups chosen from —OH (hydroxyl), —OR', wherein R' being chosen from $C_1$-$C_6$ alkyls (alkoxy), —CN, —X (halogen), —CO—, —SO$_3$H, —COOH, —OCOO—, —COO—, —OCONR—, —OCONH—, —NH—CONH—, —NR—CONR—, —CF$_3$, —CN, epoxy, —NHCO—, —N(R)CO—, wherein R is chosen from linear or branched $C_1$-$C_{22}$ alkyls optionally comprising 1-12 heteroatoms;

(iv) vinyl ethers of formula $CH_2=CHOR'_4$ or $CH_2=C(CH_3)OR'_4$, wherein $R'_4$ is chosen from linear, branched or cyclic, saturated or unsaturated, optionally aromatic, carbon-based radicals having 1 to 30 carbon atoms, optionally comprising 0 to 2 ether functional groups (—O—) and optionally 0 to 12 functional groups chosen from —OH (hydroxyl), —OR', with R' being chosen from $C_1$-$C_6$ alkyls (alkoxy), —CN, —X (halogen), —CO—, —SO$_3$H, —COOH, —OCOO—, —COO—, —OCONR—, —OCONH—, —NH—CONH—, —NR—CONR—, —CF$_3$, —CN, epoxy, —NHCO—, —N(R)CO—, wherein R is chosen from linear or branched $C_1$-$C_{22}$ alkyls optionally comprising 1-12 heteroatoms;

(v) vinyl compounds of formula $CHR''_5=CR_5R'_5$ wherein:
$R''_5$ is chosen from H and COOH, and
$R_5$ is chosen from H, CN and COOH, and
$R'_5$ is chosen from:
hydrogen, —OH, —CH=O, halogens, —COOH, —CH$_2$COOH, —NHC(O)H, —N(CH$_3$)—C(O)H, —NHC(O)CH$_3$, —N(CH$_3$)—C(O)CH$_3$;
rings chosen from:

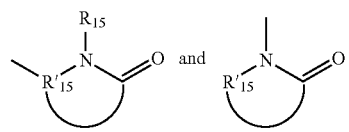

wherein $R'_{15}$ and $R_{15}$ are independently chosen from hydrogen, linear or branched, saturated or unsaturated, optionally aromatic, cyclic or non-cyclic alkyl groups, comprising 1 to 25 carbon atoms, optionally comprising heteroatoms chosen from O, N, S and P; said alkyl groups may optionally substituted by at least one substituent chosen from —OH and halogen atoms;

linear or branched alkyl groups comprising 1 to 25 carbon atoms;

$C_3$ to $C_8$ cycloalkyl groups;

$C_6$ to $C_{20}$ aryl groups;

$C_7$ to $C_{30}$ aralkyl groups, wherein alkyl having 1 to 4 carbons;

heterocyclic groups having 4 to 12 chain members containing at least one heteroatom chosen from O, N and S; and heterocycloalkyl groups, wherein alkyl having 1 to 4 carbons, wherein said alkyl, cycloalkyl, aryl, aralkyl, heterocyclic or heterocycloalkyl groups optionally comprising 0 to 2 ether functional groups (—O—) and optionally 0 to 12 functional groups chosen from —OH (hydroxyl), —OR' with R' being chosen from $C_1$-$C_6$ alkyls (alkoxy), —CN, —X (halogen), —CO—, —SO$_3$H, —COOH, —OCOO—, —COO—, —OCONR—, —OCONH—, —NH—CONH—, —NR—CONR—, —CF$_3$, —CN, epoxy, —NHCO—, —N(R)CO—, wherein R is chosen from linear or branched $C_1$-$C_{22}$ alkyl optionally comprising 1-12 heteroatoms;

and optionally substituted by at least one linear or branched, $C_1$-$C_4$ alkyl groups, optionally comprising 0 to 2 ether functional groups (—O—) and optionally 0 to 12, functional groups chosen from —OH (hydroxyl), —OR' with R' a $C_1$-$C_6$ alkyl (alkoxy), —CN, —X (halogen), —CO—, —SO$_3$H, —COOH, —OCOO—, —COO—, —OCONH—, —NH—CONH—, —CF$_3$, —CN, epoxy, —NHCO—, —N(R)CO—, wherein R is chosen from linear or branched $C_1$-$C_{22}$ alkyl optionally comprising 1-12 heteroatoms, (vii) the following anionic monomers, and salts thereof: maleic anhydride, acrylic acid, methacrylic acid, crotonic acid, itaconic acid, fumaric acid, maleic acid, 2-carboxyethyl acrylate (CH$_2$=CH—C(O)—O—(CH$_2$)$_2$—COOH), styrenesulfonic acid, 2-acrylamido-2-methylpropanesulfonic acid, vinylbenzoic acid, vinylphosphonic acid, sulfopropyl (meth)acrylate;

(viii) the following amphoteric monomers:
N,N-dimethyl-N-(2-methacryloyloxyethyl)-N-(3-sulfopropyl)ammonium betaine; N,N-dimethyl-N-(3-methacrylamidopropyl)-N-(3-sulfopropyl)ammonium betaine, and 1-(3-sulfopropyl)-2-vinylpyridinium betaine; and 2-(methacryloyloxy)ethyl phosphorylcholine;

(ix) monomers of formula:

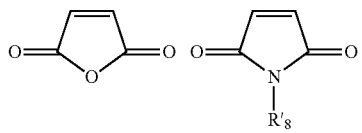

wherein R'$_8$ is chosen from H and linear or branched, saturated or unsaturated, optionally aromatic, cyclic or non-cyclic alkyl group comprising 1 to 25 carbon atoms, optionally comprising at least one heteroatoms chosen from O, N, S and P; said alkyl groups optionally by at least one chosen from —OH and halogen atoms;

(x) quaternized monomers of formula (I), quaternized monomers of formula (II) and quaternized monomers of formula (III);

(xi) multivalent compounds comprising at least two polymerizable functional groups chosen from vinyl, (meth)acrylic, allyl and (meth)acrylamide type.

15. The composition according to claim 14, wherein the at least one additional monomer is chosen from vinyl neodecanoate, vinyl tert-butylbenzoate; vinylpyrrolidone; vinylcaprolactam; N-vinylformamide; N,N'-dimethyldiallylammonium chloride; triethylammonium ethylmethacrylate chloride; ethyl, methyl, tert-butyl or isobornyl (meth)acrylate; vinyl acetate, crotonic acid; (meth)acrylic acid, methacryloyl ethyl betaine, octylacrylamide; N-methyl-N-vinylimidazolinium chloride, 1-eicosene, tert-butylacrylamide, acrylamide, and hexadecene.

16. The composition according to claim 1, wherein the at least one cationic ethylenic polymer is chosen from:
poly(vinylpyrrolidone-co-dimethylaminoethyl methacrylate) copolymers;
poly(vinylcaprolactam-co-vinylpyrrolidone-co-dimethylaminoethyl methacrylate) copolymers;
poly(vinylpyrrolidone-co-dimethylaminopropyl methacrylamide) copolymers;
poly(vinylpyrrolidone-co-polyvinylcaprolactam-co-dimethylaminopropyl methacrylamide) copolymers;
poly(vinylamine), poly(allylamine), poly(diallylamine); and
poly(N-vinylformamide-co-vinylamine) copolymers.

17. The composition according to claim 1, wherein the at least one cationic ethylenic polymer comprises at least 3 repeating units chosen from:

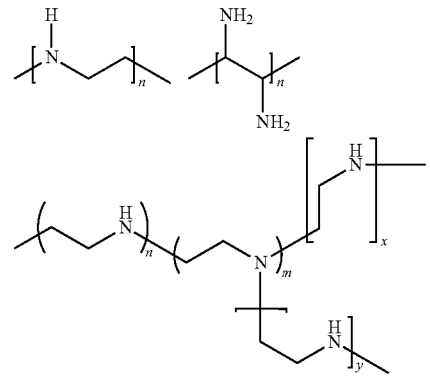

18. The composition according to claim 1, wherein the at least one neutralizing agent is present in an amount ranging from 0.01 to 3 molar equivalents relative to the total amine functional groups of the at least one cationic ethylenic polymer.

19. A method for treating keratinous substances chosen from the skin of the body or face, nails, hairs, eyelashes and eyebrows, comprising applying to said keratinous substances the cosmetic composition according to claim 1.

* * * * *